United States Patent
Martinez et al.

(10) Patent No.: US 9,044,464 B2
(45) Date of Patent: Jun. 2, 2015

(54) NO-RELEASING GUANIDINE-COXIB ANTI-CANCER AGENTS

(71) Applicant: Euclises Pharmaceuticals, Inc., St. Louis, MO (US)

(72) Inventors: Eduardo J. Martinez, Bryn Mawr, PA (US); John J. Talley, St. Louis, MO (US); Terri L. Boehm, Ballwin, MO (US)

(73) Assignee: EUCLISES PHARMACEUTICALS, INC., St. Louis, MO (US)

( * ) Notice: Subject to any disclaimer, the term of this patent is extended or adjusted under 35 U.S.C. 154(b) by 166 days.

(21) Appl. No.: 13/940,907

(22) Filed: Jul. 12, 2013

(65) Prior Publication Data
US 2014/0018403 A1 Jan. 16, 2014

Related U.S. Application Data

(60) Provisional application No. 61/670,916, filed on Jul. 12, 2012.

(51) Int. Cl.
*A61K 31/415* (2006.01)
*C07D 231/12* (2006.01)
*A61K 45/06* (2006.01)

(52) U.S. Cl.
CPC ............ *A61K 31/415* (2013.01); *C07D 231/12* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,760,068 A | 6/1998 | Talley et al. | 514/403 |
| 8,143,237 B2 | 3/2012 | Gokaraju et al. | C07D 517/04 |
| 2013/0190324 A1 | 7/2013 | Kompella et al. | A61K 47/48038 |

FOREIGN PATENT DOCUMENTS

EP 1 336 602 8/2003

OTHER PUBLICATIONS

Anning et al. (2006). "Nitric oxide deficiency promotes vascular side effects of cyclooxygenase inhibitors." *Bloodjournal* 108:4059-4062.
Bertagnolli et al. (2009). "Five year efficacy and safety analysis of the adenoma prevention with celecoxib (APC) trial." *Cancer Prev Res (Phila)* 2(4):310-321.
Carie et al. (2011). IT-141, a polymer micelle encapsulating sn-38, induces tumor regression in multiple colorectal cancer models. *Journal of Drug Delivery* 1-9 (Article ID 869027).
Ellis et al. (2005). "NMI-1182, a gastro-protective cyclo-oxygenase-inhibiting nitric oxide donor." *Inflammopharmacology*, 12(5-6):521-534.
Hida et al. (2000). "Cyclooxygenase-2 inhibitor induces apoptosis and enhances cytotoxicity of various anticancer agents in non-small cell lung cancer cell lines." *Clinical Cancer Research.* 6:2006-2011.
Higashi et al. (1999). "Effect of L-arginine infusion on systemic and renal hemodynamics in hypertensive patients." *American Journal of Hypertension.* 12:8-15.
Jiménez et al. (2004). "Role of L-arginine in ibuprofen-induced oxidative stress and neutrophil infiltration in gastric mucosa." *Free Radical Research* 38(9):903-911.
Kashfi et al. (2002). "Nitric oxide-donating nonsteroidal anti-inflammatory drugs inhibit the growth of various cultured human cancer cells: evidence of a tissue type-independent effect." *The Journal of Pharmacology and Experimental Therapeutics* 303:1273-1282.
Kiguchi et al. (2007). "Therapeutic effect of CS-706, a specific cyclooxygenase-2 inhibitor, on gallbladder carcinoma in BK5.ErbB-2 mice." *Mol Cancer Ther* 6:1709-1717.
Martin et al. (2008) "Preparation of NG-Substituted L-Arginine Analogues Suitable for Solid Phase Peptide Synthesis." *J. Org. Chem.* 73(19):7849-7851.
Muscará et al. (1998). "Effect of a nitric oxide-releasing naproxen derivative on hypertension and gastric damage induced by chronic nitric oxide inhibition in the rat." *Life Sciences* 62(15):235-240.
Ouyang et al. (2003). "Nitric oxide-donating aspirin prevents pancreatic cancer in a hamster tumor model." *Cancer Research* 66:4503-4511.
Park et al. (2010). "Suppression of A549 lung cancer cell migration by precursor let-7g microRNA." *Mol. Med. Reports* 3:1007-1013.
Penning et al. (1997). "Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benzenesulfonamide (SC-58635, celecoxib)." *J. Med. Chem.* 40:1347-1365.
Rao et al. (2006). "Nitric oxide-releasing aspirin and indomethacin are potent inhibitors against colon cancer in azoxymethane-treated rats: effects on molecular targets." *Mol. Cancer Ther.* 5:1530-1538.
Steele et al. (2009). "Chemopreventive efficacy of naproxen and nonaproxen in rodent models of colon, urinary bladder, and mammary cancers." *Cancer Prev Res (Phila)* 2:951-956.
Whittle. (2003). "Nitric oxide and the gut injury induced by non-steroidal anti-inflammatory drugs." *Inflammopharmacology* 11(4):415-22. (Abstract Only).
Williams et al. (2001). "Squalamine treatment of human tumors in nu/nu mice enhances platinum-based chemotherapies." *Clinical Cancer Research* 7:724-733.

*Primary Examiner* — Kamal Saeed
(74) *Attorney, Agent, or Firm* — Harness, Dickey & Pierce, P.L.C.

(57) ABSTRACT

The present disclosure provides NO-releasing guanidine-coxib anti-cancer agents, having the structure of Formula (I):

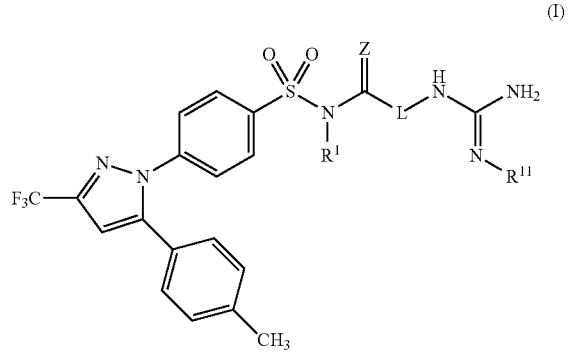

wherein $R^1$, $R^{11}$, Z and L are as defined in the detailed description; pharmaceutical compositions comprising at least one of the compounds of Formula (I); and methods useful for healing wounds, preventing and treating cancer, or treating actinic keratosis, cystic fibrosis, acne, or a disease mediated by arginine deficiency using a compound of Formula (I).

19 Claims, No Drawings

NO-RELEASING GUANIDINE-COXIB ANTI-CANCER AGENTS

CROSS-REFERENCE TO RELATED APPLICATIONS

This application claims the benefit of U.S. Provisional Application No. 61/670,916, filed on 12 Jul. 2012. The entire disclosure of the above application is incorporated herein by reference.

FIELD

The present invention generally relates to NO-releasing coxib compounds, pharmaceutical compositions comprising the compounds, methods useful for treating a subject by administering a therapeutically effective amount of the compounds, and methods for making the compounds. More specifically, the present invention relates to a class of NO-releasing guanidine-coxib cardioprotective compounds, pharmaceutical compositions thereof, and methods useful for healing wounds, preventing and treating cancer, and treating actinic keratosis, cystic fibrosis and acne.

BACKGROUND

Despite decades of effort, cancer remains an especially difficult disease for development of therapeutics. According to the Cancer Prevention Coalition (University of Illinois), cancer rates have increased 24% in the past thirty years even after adjusting for aging of the population. Remarkably, despite significant progress during this period the overall five-year survival rates have remained virtually static (approximately 50% depending on the cancer). Thus new drugs are required to develop more effective life-saving cancer therapies.

Celecoxib, a selective COX-2 inhibitor, is one of the world's most successful drugs, alleviating pain and inflammation for millions of patients. In addition, COX-2 overexpression has been found in several types of human cancers such as colon, breast, lung, prostate and pancreas, and appears to control many cellular processes. COX-2 plays a role in carcinogenesis, apoptosis and angiogenesis, and therefore represents an excellent drug target for the development of novel medicines for prevention and/or treatment of human cancers. Currently, celecoxib is approved for limited use in the reduction of polyps in familial adenomatous polyposis (FAP).

The Adenoma Prevention with Celecoxib (APC) trial demonstrated human efficacy of celecoxib in the prevention of sporadic colorectal adenoma. However, this trial also showed that the elevated dose of celecoxib required for anti-cancer efficacy was accompanied by concomitant increase in adverse cardiovascular (CV) events (Bertagnolli, et al., *Cancer Prev. Res.* (Phila) 2, 310-321 (2009)).

Development of more potent or selective COX-2 inhibitors does not improve CV safety; this liability is thought to be a mechanism-based effect. This was demonstrated in the VIGOR trial by Vioxx®, an extremely potent and highly selective COX-2 inhibitor withdrawn from the market in 2004 due to CV concerns about increased risk of heart attack and stroke with long term, high dose use. These facts have undermined the development of novel COX-2 inhibitors and slowed research to expand their utility to other disease indications, such as cancer.

Nitric oxide (NO) is an important endogenous signaling molecule and vasodilator. NO is synthesized from L-arginine by the enzyme NO synthase (NOS), which exists in three distinct isoforms, namely the constitutively expressed endothelial (eNOS) and neuronal (nNOS) forms, and the mainly inducible form (iNOS). Arginine administration has been shown to reduce blood pressure and renal vascular resistance in essential hypertensive patients with normal or insufficient renal function (*Am. J. Hypertens.* 12, 8-15 (1999)). It has also been shown that NO deficiency promotes vascular side-effects of celecoxib and other COX inhibitors (Blood 108, 4059-4062 (2006)).

The role of NO in cancer is complex; however, pharmacological evidence using NO-releasing compounds of NSAID's has shown increased anti-tumor efficacy in cell culture and animal cancer models. The different molecular mechanisms of NO are expected to simultaneously enhance anti-cancer efficacy of celecoxib and improve CV safety by preventing an increase in blood pressure associated with COX-2 inhibition, while maintaining gastric-sparing properties superior to NSAID's.

Diverse molecular mechanisms of NO delivery are well known. For example, Kashfi, et al. reported that nitric oxide-donating nonsteroidal anti-inflammatory drugs (NO-sulindac, NO-ibuprofen, NO-indomethacin and NO-aspirin) inhibit the growth of various cultured human cancer cells; providing evidence of a tissue type-independent effect (*J. Pharmacol. Exp. Ther.* 303, 1273-1282 (2002)).

In another example, Ouyang, et al. reported that nitric oxide-donating aspirin prevented pancreatic cancer in a hamster tumor model (*Cancer Res.* 66, 4503-4511 (2006)).

COX inhibition and cancer: Two isoforms of cyclooxygenase (COX) are known to exist, a constitutive form (COX-1) present in nearly all tissues and an inducible form (COX-2) upregulated in response to inflammatory stimuli. The discovery of COX-2 led to the development of selective COX-2 inhibitors as anti-inflammatory drugs (coxibs), which were shown to be largely devoid of antiplatelet activity and gastrointestinal ulcerogenicity believed to be associated with inhibition of COX-1.

NSAID's are among the most widely used treatments for pain, fever and inflammation, and have long been known to reduce the risk of cancer in multiple organ sites. The use of aspirin in treatment and prevention of cancer has wide-spread support in the medical community; however, the risks of regular aspirin use are also well established and the risk-benefit profile is not sufficient to recommend aspirin treatment for cancer prevention. With the advent of coxibs, research has focused on COX-2 as a target for the treatment and prevention of certain cancers. Compelling data from the APC trial, described above, demonstrated that celecoxib was useful in preventing sporadic colorectal adenoma in patients at high risk for colorectal cancer.

The role of COX-2 in lung cancer: Lung cancer is the leading cause of cancer-related deaths in the US and is responsible for more deaths than breast, prostate and colon cancers combined. Current research suggests that COX-2 and epidermal growth factor receptor, (EGFR), are important mediators in non-small cell lung cancer (NSCLC). In human NSCLC patients, a combination of erlotinib (a tyrosine kinase inhibitor), and celecoxib showed high response rates and demonstrable clinical benefit. NSCLC currently represents one of the preferred indications for COX-2 inhibition cancer therapy.

Mechanism of COX-2 in cancer: A key feature of COX-2 biology is its ability alone to cause cancer formation in a number of transgenic mouse models. COX-2 derived $PGE_2$ plays a prominent role in tumor growth and the most abundant prostanoid in many human malignancies. Metabolism of arachidonic acid by COX-2 leads to the formation of several prostaglandins (PGs) that bind to tumor suppressor p53, preventing p53-mediated apoptosis. COX-2 derived $PGE_2$ promotes epithelial-to-mesenchymal transition and thus increases resistance to EGFR tyrosine kinase inhibitors in lung cancer.

Nitric oxide and cardiovascular safety: Nitric oxide exhibits a number of important pharmacological actions including vascular relaxation (vasodilatation) and inhibition of platelet aggregation and adhesion. Inhibition of NO synthesis leads to an increase in systemic blood pressure. NO also prevents atherogenesis by inhibiting vascular smooth muscle cell proliferation and preventing low-density lipoprotein oxidation and macrophage activation. Vascular NO generation is important in controlling blood pressure, and a growing body of evidence indicates that NO signaling is a key factor in counteracting the onset and development of several CV diseases including hypertension, myocardial infarction and stroke. NO can be used to counteract CV liabilities associated with COX-2 inhibition.

Nitric oxide and gastric sparing properties: NO-releasing COX inhibitors were originally created to improve gastrointestinal (GI) tolerability (*Inflammopharmacology* 11(4), 415-22 (2003)). Naproxcinod is a NO-releasing pro-drug of the NSAID naproxen. Naproxcinod showed significantly improved GI tolerability compared to naproxen alone in a chronic rat study (Life Sciences 62, 235-240 (1998)). In another example, L-arginine, coadministered with the NSAID ibuprofen, showed a protective effect on gastric mucosa against ibuprofen-induced mucosal lesions (*Free Radic. Res.* 38(9), 903-11 (2004)).

Nitric oxide and cancer: NO modulates the activity of transcription factor NF-κB, which represents a potential mechanism for inflammation control, but also regulation of apoptotic mechanisms. NO promotes apoptosis and can reverse tumor cell resistance to chemotherapeutic agents. Studies with NO-releasing NSAID's have shown that NO contributes to anti-cancer activity in cell culture and enhanced in vivo efficacy in rodent cancer models. For example, Steele, et al. reported the chemopreventive efficacy of nitric oxide-naproxen in rodent models of colon, urinary bladder and mammary cancers (*Cancer Prev. Res.* (Phila) 2, 951-956 (2009)).

Nitrate prodrugs useful in the treatment of inflammatory, ischemic, degenerative and proliferative diseases are reported in EP 01336602 (published 20 Aug. 2003). The compounds described therein include celecoxib coupled with one of the following: nitrooxyalkylenecarbonyl; methylimine-aminomethylene-phenylenemethylene-amide-ethylenecarbonyl; or fluoromethylimine-aminomethylene-phenylenemethylene-amide-ethylenecarbonyl to sulfonamide nitrogen yielding, respectively, Structures (1)-(3) below:

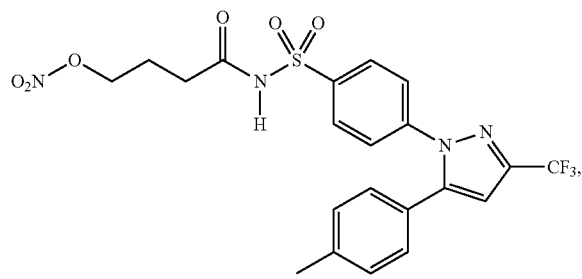

(1)

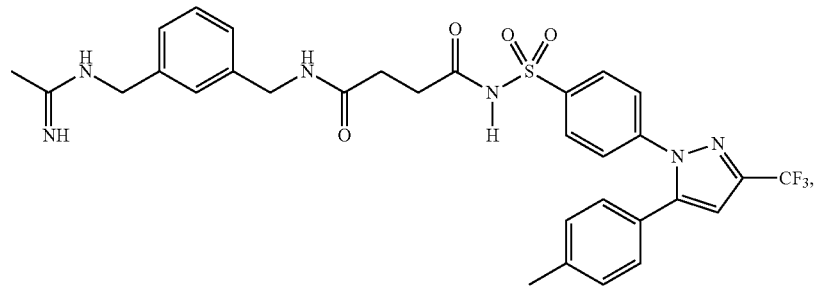

(2)

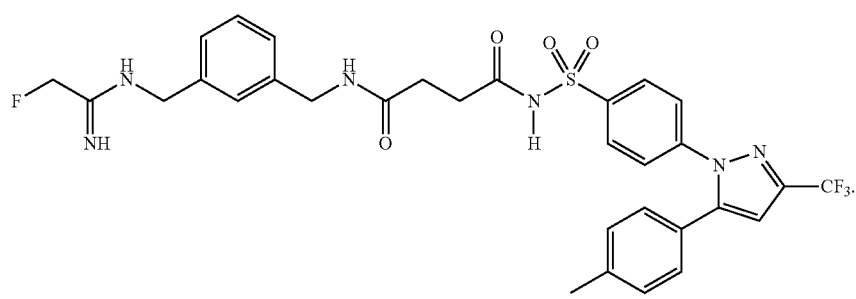

(3)

SUMMARY OF THE INVENTION

Herein described is a family of NO-releasing coxib conjugates which provides a therapeutic benefit to a subject with a disease indication, such as cancer, actinic keratosis, cystic fibrosis, acne, or a disease mediated by arginine deficiency, or provides a wound healing benefit to a subject. Such NO-releasing coxib conjugate can improve CV safety, permit higher dose of cancer-treating compound, enhance cancer-treating efficacy, and/or maintain gastric-sparing properties superior to NSAID's.

In an embodiment, there is provided a compound of Formula (I):

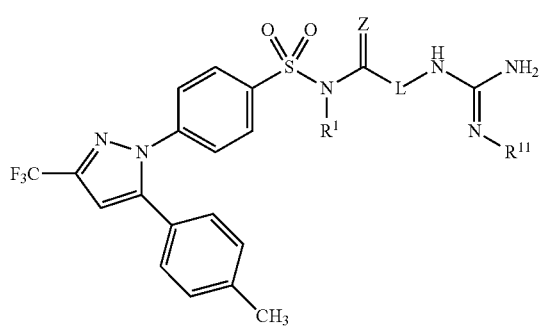

and pharmaceutically acceptable salts thereof, wherein $R^1$, $R^{11}$, Z and L are as defined in the detailed description.

Compounds of the present invention can exist in tautomeric, geometric or stereoisomeric forms. An ester, metabolite, oxime, prodrug, onium, hydrate, solvate and N-oxide forms of a compound of Formula (I) are also embraced by the invention. The present invention considers all such compounds, including, but not limited to, cis- and trans-geometric isomers (Z- and E-geometric isomers), R- and S-enantiomers, diastereomers, d-isomers, l-isomers, atropisomers, epimers, conformers, rotamers, mixtures of isomers and racemates thereof, as falling within the scope of the invention.

In another embodiment, there is provided a pharmaceutical composition comprising a compound of Formula (I) and a pharmaceutically-acceptable carrier.

In another embodiment, the pharmaceutical composition further comprises one or more additional pharmaceutically active compounds.

In another embodiment, there is provided a method for treating or preventing a disease condition comprising administering to a subject a therapeutically effective amount of a compound of Formula (I), wherein the condition to be treated or prevented includes, for example, cancer. Further non-limiting examples include non-small cell lung cancer, skin cancer, liver cancer, colorectal cancer (including metastatic colorectal cancer and FAP), glioblastoma (and other CNS related cancers), squamous cell cancer, bladder cancer, breast cancer, biliary tract cancer, cervical cancer, prostate cancer, small cell lung cancer, ovarian cancer, pancreatic cancer, gastrointestinal cancer and CNS cancer.

In another embodiment, there is provided a method for healing wounds, comprising administering to a subject a therapeutically effective amount of a compound of Formula (I).

In another embodiment, there is provided a method for treating a condition, comprising administering to a subject a therapeutically effective amount of a compound of Formula (I), wherein the condition to be treated includes, for example, actinic keratosis, cystic fibrosis and/or acne.

In another embodiment, there is provided a method for treating a condition comprising administering to a subject a therapeutically effective amount of a compound of Formula (I), wherein the condition to be treated includes, for example, autoimmune disorder, inflammatory disorder and/or auto-inflammatory disorder.

In another embodiment, there is provided a method for treating a condition comprising administering to a subject a therapeutically effective amount of a compound of Formula (I), wherein the condition to be treated includes, for example, elevated level of arginase.

In another embodiment, there is provided a method that comprises administering a combination of a compound of Formula (I) and at least one additional pharmaceutically active compound.

In another embodiment, there is provided a use of a compound of Formula (I) for manufacture of a medicament for treatment of a disease condition in a subject.

In another embodiment, there is provided a method for preparing a compound of Formula (I).

In another embodiment, there is provided an intermediate useful in making a compound of Formula (I).

In another embodiment, there is provided a method of enhancing cancer-treating efficacy by activating both NO and COX-2-inihibitor anti-tumor mechanisms in a subject, by administering a therapeutically effective amount of a compound of Formula (I).

In another embodiment, there is provided a method of treating a subject suffering from a disease condition caused by COX-2 over-expression, including but not limited to cancer, by administering a therapeutically effective amount of a compound of Formula (I).

In another embodiment, there is provided a method of improving CV safety in a subject, by administering a therapeutically effective amount of a compound of Formula (I).

In another embodiment, there is provided a method of treating a subject suffering from a disease condition, including but not limited to cancer, by administering a high-dose of a compound of Formula (I).

In another embodiment, there is provided a method of cardio-protection in a subject, comprising administering a therapeutically effective amount of a compound of Formula (I).

In another embodiment, there is provided a method of releasing NO in a subject, comprising administering a therapeutically effective amount of a compound of Formula (I).

In another embodiment, there is provided a method of cardio-protection in a subject, comprising administering a therapeutically effective amount of a compound of Formula (I), which releases NO in the subject, preferably by sustained release.

In another embodiment, there is provided a method of cardio-protection in a subject, comprising administering a therapeutically effective amount of a compound of Formula (I), which releases NO in the subject, preferably by sustained release.

In another embodiment, there is provided a method of cardio-protection in a subject, comprising administering a therapeutically effective amount of a compound of Formula (I), which releases NO in the subject, preferably by sustained release, wherein NO release proceeds through an enzymatic pathway involving a guanidine moiety of a compound of Formula (I).

In another embodiment, there is provided a method of cardio-protection in a subject, comprising administering a therapeutically effective amount of a compound of Formula (I), which releases NO in the subject, preferably by sustained release, wherein NO release proceeds through a non-enzymatic pathway involving a guanidine moiety of a compound of Formula (I).

In another embodiment, there is provided a method of treating a subject suffering from a disease condition, including but not limited to cancer, comprising administering a therapeutically effective amount of a compound of Formula (I), without causing substantial adverse, cardiovascular events.

In another embodiment, there is provided a method of treating a subject suffering from a disease condition, including but not limited to cancer, comprising administering a therapeutically effective amount of a compound of Formula (I), without causing substantial changes in blood pressure, while maintaining gastric-sparing properties.

DETAILED DESCRIPTION

A. Compounds

A compound, or a pharmaceutically acceptable salt, or solvate of a compound or salt, of Formula (I):

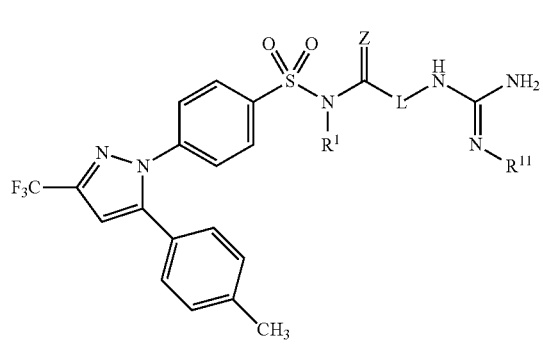

wherein, $R^1$ is selected from the group consisting of H, OH, alkyl, and alkoxyalkyl; $R^{11}$ is H or hydroxy; Z is selected from the group consisting of O and S; -L- is $C_{1-15}$ alkylene, wherein one or more —$CH_2$— radicals are optionally replaced with a radical independently selected from the group consisting of: —$CH(R^4)$—, —$CH(R^4)$—O—, —$C(R^4)_2$—,

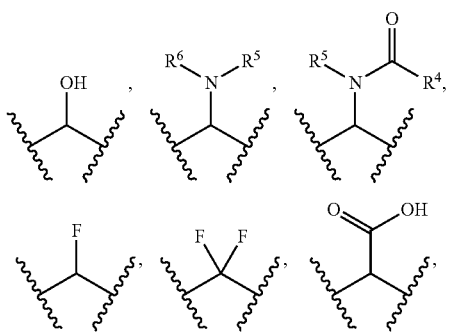

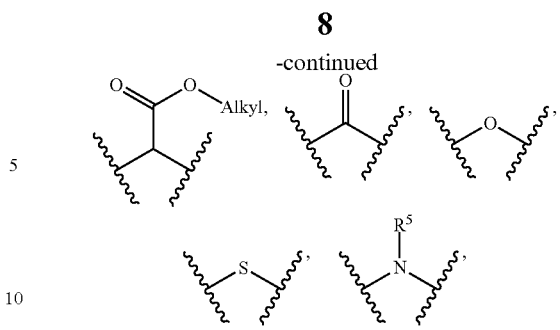

$R^4$ is selected from the group consisting of H, alkyl, acyl, acylamino, amino, aryl, heterocyclyl, alkoxy, alkylthio, alkyl-NH—, or $R^4$ is taken together with $R^5$ or $R^6$ to form a cyclic ring; $R^5$ is selected from the group consisting of H, alkyl, hydroxyalkyl, aryl, heterocyclyl, alkylcarbonyl, arylcarbonyl, heterocyclylcarbonyl, carboxyalkylcarbonyl, alkyloxycarbonylalkylcarbonyl, alkylsulfonyl, arylsulfonyl and heteroarylsulfonyl, or $R^5$ is taken together with $R^4$ or $R^6$ to form a cyclic ring; and $R^6$ is selected from the group consisting of H, alkyl, hydroxyalkyl, aryl, heterocyclyl, alkylcarbonyl, arylcarbonyl, heterocyclylcarbonyl, carboxyalkylcarbonyl, alkyloxycarbonylalkylcarbonyl, alkylsulfonyl, arylsulfonyl and heteroarylsulfonyl, or $R^6$ is taken together with $R^4$ or $R^5$ to form a cyclic ring.

In another family of the compounds of Formula (I), $R^1$ is selected from the group consisting of H, alkyl and alkoxyalkyl; $R^{11}$ is H or hydroxy; Z is selected from the group consisting of O and S; -L- is $C_{1-10}$ alkylene, wherein one or more —$CH_2$— radicals are optionally replaced with a radical independently selected from the group consisting of —$CH(R^4)$—, —$CH(R^4)$—O—, —$C(R^4)_2$—,

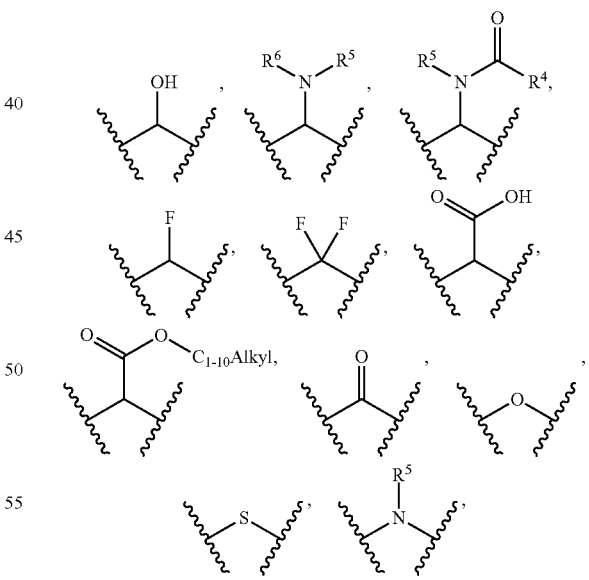

$R^4$ is selected from the group consisting of H, $C_{1-10}$ alkyl, acyl, acylamino, amino, aryl, heterocyclyl, $C_{1-10}$ alkoxy, $C_{1-10}$ alkylthio and $C_{1-10}$ alkyl-NH—, or $R^4$ may be taken together with $R^5$ or $R^6$ to form a cyclic ring; $R^5$ is selected from the group consisting of H, $C_{1-10}$ alkyl, aryl, heteroaryl, $C_{1-10}$ alkylsulfonyl, arylsulfonyl and heteroarylsulfonyl, or $R^5$ may be taken together with $R^4$ or $R^6$ to form heterocyclyl; and $R^6$ is selected from the group consisting of H, $C_{1-10}$ alkyl, aryl, heteroaryl, $C_{1-10}$ alkylsulfonyl, arylsulfonyl and heteroarylsulfonyl, or $R^6$ may be taken together with $R^4$ or $R^5$ to form heterocyclyl.

In another family of the compounds of Formula (I), $R^1$ is selected from the group consisting of H, alkyl and alkoxyalkyl; Z is selected from the group consisting of O and S; -L- is $C_{1-8}$ alkylene, wherein one or more —$CH_2$— radicals are optionally replaced with a radical independently selected from the group consisting of —$CH(R^4)$—, —$CH(R^4)$—O—, —$C(R^4)_2$—,

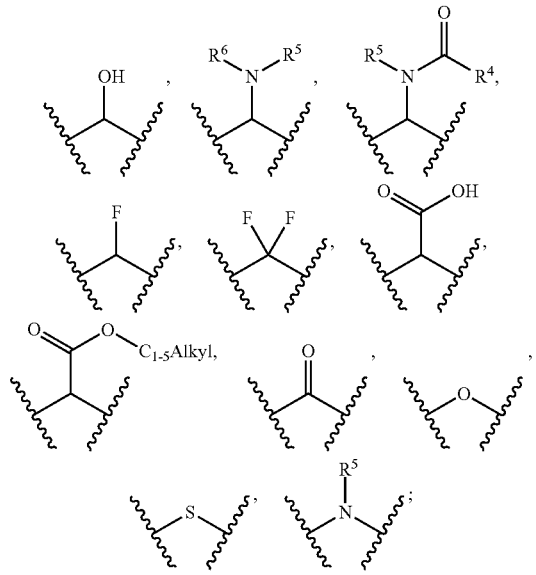

$R^4$ is independently selected from the group consisting of H, $C_{1-6}$ alkyl, acyl, acylamino, amino, aryl, heterocyclyl, $C_{1-6}$ alkoxy, $C_{1-6}$ alkylthio and $C_{1-6}$ alkyl-NH—; $R^5$ is independently selected from the group consisting of H, $C_{1-6}$ alkyl, aryl, heteroaryl, $C_{1-6}$ alkylsulfonyl, arylsulfonyl and heteroarylsulfonyl; and $R^6$ is independently selected from the group consisting of H, $C_{1-6}$ alkyl, aryl, heteroaryl, $C_{1-6}$ alkylsulfonyl, arylsulfonyl and heteroarylsulfonyl.

In another family of the compounds of Formula (I), $R^1$ is H; $R^{11}$ is H or hydroxy; Z is selected from the group consisting of O and S; -L- is $C_{1-8}$ alkylene, wherein one or more —$CH_2$— radicals may be replaced with a radical independently selected from the group consisting of —$CH(R^4)$—, —$CH(R^4)$—O— and —$C(R^4)_2$—; and $R^4$ is independently selected from the group consisting of H, $C_{1-6}$ alkyl, acetylamino, amino, aryl and phthalimido.

In another family of the compounds of Formula (I), $R^1$ is H; $R^{11}$ is H or hydroxy; Z is selected from the group consisting of O and S; -L- is $C_{1-8}$ alkylene, wherein one —$CH_2$— radical is optionally replaced with —$CH(R^4)$—; and $R^4$ is independently selected from the group consisting of acetylamino and amino.

In another family of the compounds of Formula (I) useful in investigating the structure-activity relationship of compounds of the present invention, $R^1$ is H; $R^{11}$ is H or hydroxy; Z is O; -L- is $C_{1-8}$ alkylene. Non-limiting examples include:

TABLE 1

| No. | Compound Name |
|---|---|
| 1 | 5-guanidino-N-((4-(5-(p-tolyl)-3-(trifluoromethyl)-1H-pyrazol-1-yl)phenyl)sulfonyl)pentanamide |
| 2 | 2-guanidino-N-((4-(5-(p-tolyl)-3-(trifluoromethyl)-1H-pyrazol-1-yl)phenyl)sulfonyl)acetamide |
| 3 | 3-guanidino-N-((4-(5-(p-tolyl)-3-(trifluoromethyl)-1H-pyrazol-1-yl)phenyl)sulfonyl)propanamide |
| 4 | 4-guanidino-N-((4-(5-(p-tolyl)-3-(trifluoromethyl)-1H-pyrazol-1-yl)phenyl)sulfonyl)butanamide |

In another family of the compounds of Formula (I), $R^1$ is H; $R^{11}$ is H or hydroxy; Z is O; -L- is $C_{1-8}$ alkylene, wherein one —$CH_2$— radical is replaced with —$CH(R^4)$—; and $R^4$ is selected from the group consisting of H, $C_{1-6}$ alkyl, acylamino, amino, aryl and phthalimido.

In another family of the compounds of Formula (I), $R^1$ is H; $R^{11}$ is H or hydroxy; Z is O; -L- is $C_{1-8}$ alkylene, wherein one —$CH_2$— radical is replaced with —$CH(R^4)$—; and $R^4$ is selected from the group consisting of acetylamino and amino.

The present invention is also directed to a subclass of compounds, including pharmaceutically acceptable salts of compounds, wherein compounds have the structure of Formula (II):

(II)

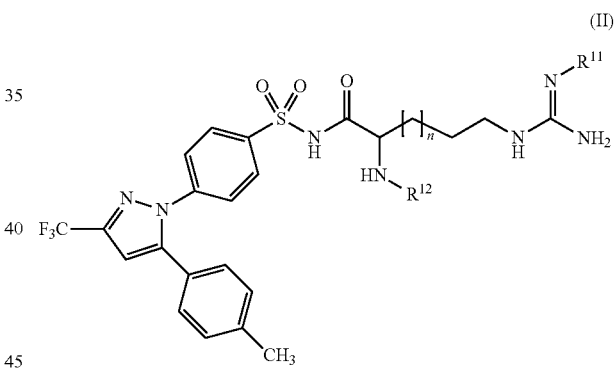

wherein: n is 1, 2, 3 or 4; $R^{11}$ is H or hydroxy; and $R^{12}$ is selected from the group consisting of H, alkyl, aryl, heteroaryl, arylalkyl, alkoxy, aryloxy, heteroaryloxy, cycloalkyl, heterocycloalkyl, acyl and aroyl.

In a family of the compounds of Formula (II), n is 1 or 2; $R^{11}$ is H; and $R^{12}$ is selected from the group consisting of H, alkyl, aryl, heteroaryl, arylalkyl, alkoxy, aryloxy, heteroaryloxy, cycloalkyl, heterocycloalkyl, acyl and aroyl.

In another family of the compounds of Formula (II), n is 1 or 2; $R^{11}$ is H; and $R^{12}$ is selected from the group consisting of H, acyl and aroyl. Non-limiting examples include:

TABLE 2

| No. | Compound Name |
|---|---|
| 5 | (S)-2-Amino-5-guanidino-N-((4-(5-(p-tolyl)-3-(trifluoromethyl)-1H-pyrazol-1-yl)phenyl)sulfonyl)pentanamide |
| 6 | (S)-2-Acetamido-5-guanidino-N-((4-(5-(p-tolyl)-3-(trifluoromethyl)-1H-pyrazol-1-yl)phenyl)sulfonyl)pentanamide |

TABLE 2-continued

| No. | Compound Name |
|---|---|
| 7 | (S)-2-Formamido-5-guanidino-N-((4-(5-(p-tolyl)-3-(trifluoromethyl)-1H-pyrazol-1-yl)phenyl)sulfonyl)pentanamide |
| 8 | (S)-5-Guanidino-2-propionamido-N-((4-(5-(p-tolyl)-3-(trifluoromethyl)-1H-pyrazol-1-yl)phenyl)sulfonyl)pentanamide |
| 9 | (S)-N-(5-Guanidino-1-oxo-1-(4-(5-(p-tolyl)-3-(trifluoromethyl)-1H-pyrazol-1-yl)phenylsulfonamido)pentan-2-yl)benzamide |
| 10 | (S)-2-Amino-6-guanidino-N-((4-(5-(p-tolyl)-3-(trifluoromethyl)-1H-pyrazol-1-yl)phenyl)sulfonyl)hexanamide |
| 11 | (S)-2-Acetamido-6-guanidino-N-((4-(5-(p-tolyl)-3-(trifluoromethyl)-1H-pyrazol-1-yl)phenyl)sulfonyl)hexanamide |
| 12 | (S)-2-Formamido-6-guanidino-N-((4-(5-(p-tolyl)-3-(trifluoromethyl)-1H-pyrazol-1-yl)phenyl)sulfonyl)hexanamide |
| 13 | (S)-6-Guanidino-2-propionamido-N-((4-(5-(p-tolyl)-3-(trifluoromethyl)-1H-pyrazol-1-yl)phenyl)sulfonyl)hexanamide |
| 14 | (S)-N-(6-Guanidino-1-oxo-1-(4-(5-(p-tolyl)-3-(trifluoromethyl)-1H-pyrazol-1-yl)phenylsulfonamido)hexan-2-yl)benzamide |

In another family of compounds of Formula (II), n is 1 or 2; $R^{11}$ is hydroxy; and $R^{12}$ is selected from the group consisting of H, alkyl, aryl, heteroaryl, arylalkyl, alkoxy, aryloxy, heteroaryloxy, cycloalkyl, heterocycloalkyl, acyl, and aroyl.

In another family of compounds of Formula (II), n is 1 or 2; $R^{11}$ is hydroxy; and $R^{12}$ is selected from the group consisting of H, acyl, and aroyl. Non-limiting examples include:

TABLE 3

| No. | Compound Name |
|---|---|
| 15 | (S)-2-Amino-5-(2-hydroxyguanidino)-N-((4-(5-(p-tolyl)-3-(trifluoromethyl)-1H-pyrazol-1-yl)phenyl)sulfonyl)pentanamide |
| 16 | (S)-2-Acetamido-5-(2-hydroxyguanidino)-N-((4-(5-(p-tolyl)-3-(trifluoromethyl)-1H-pyrazol-1-yl)phenyl)sulfonyl)pentanamide |
| 17 | (S)-2-formamido-5-(2-hydroxyguanidino)-N-((4-(5-(p-tolyl)-3-(trifluoromethyl)-1H-pyrazol-1-yl)phenyl)sulfonyl)pentanamide |
| 18 | (S)-5-(2-hydroxyguanidino)-2-propionamido-N-((4-(5-(p-tolyl)-3-(trifluoromethyl)-1H-pyrazol-1-yl)phenyl)sulfonyl)pentanamide |
| 19 | (S)-N-(5-(2-hydroxyguanidino)-1-oxo-1-(4-(5-(p-tolyl)-3-(trifluoromethyl)-1H-pyrazol-1-yl)phenylsulfonamido)pentan-2-yl)benzamide |
| 20 | (S)-2-Amino-6-(2-hydroxyguanidino)-N-((4-(5-(p-tolyl)-3-(trifluoromethyl)-1H-pyrazol-1-yl)phenyl)sulfonyl)hexanamide |
| 21 | (S)-2-Acetamido-6-(2-hydroxyguanidino)-N-((4-(5-(p-tolyl)-3-(trifluoromethyl)-1H-pyrazol-1-yl)phenyl)sulfonyl)hexanamide |
| 22 | (S)-2-Formamido-6-(2-hydroxyguanidino)-N-((4-(5-(p-tolyl)-3-(trifluoromethyl)-1H-pyrazol-1-yl)phenyl)sulfonyl)hexanamide |
| 23 | (S)-6-(2-Hydroxyguanidino)-2-propionamido-N-((4-(5-(p-tolyl)-3-(trifluoromethyl)-1H-pyrazol-1-yl)phenyl)sulfonyl)hexanamide |
| 24 | (S)-N-(6-(2-Hydroxyguanidino)-1-oxo-1-(4-(5-(p-tolyl)-3-(trifluoromethyl)-1H-pyrazol-1-yl)phenylsulfonamido)hexan-2-yl)benzamide |

B. Definitions

The terms "substituent", "radical", "group", "moiety" and "fragment" may be used interchangeably.

The term "hydrido" denotes a single —H atom (H) and may be used interchangeably with the symbol "H". Hydrido may be attached, for example, to an oxygen atom to form a "hydroxy" radical (i.e., —OH), or two hydrido radicals may be attached to a carbon atom to form a "methylene" (—CH₂—) radical.

The terms "hydroxyl" and "hydroxy" may be used interchangeably.

If a substituent is described as being "optionally substituted," the substituent may be either (1) not substituted or (2) substituted on a substitutable position. If a substitutable position is not substituted, the default substituent is H.

Singular forms "a" and "an" may include plural reference unless the context clearly dictates otherwise.

The number of carbon atoms in a substituent can be indicated by the prefix "$C_{A-B}$" where A is the minimum and B is the maximum number of carbon atoms in the substituent.

The term "halo" refers to fluoro (—F), chloro (—Cl), bromo (—Br), or iodo (—I).

The term "alkyl" denotes a linear or branched acyclic alkyl radical containing from 1 to about 15 carbon atoms. In some embodiments, alkyl is a $C_{1-10}$ alkyl, $C_{1-7}$ alkyl, $C_{1-6}$ alkyl or $C_{1-5}$ alkyl radical. Examples of alkyl include, but are not limited to, methyl, ethyl, propyl, isopropyl, butyl, isobutyl, tert-butyl, sec-butyl, pentan-3-yl

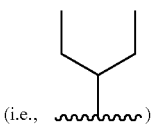

(i.e., )

and the like.

The term "alkylcarbonyl" denotes an alkyl radical attached to carbonyl.

The term "hydroxyalkyl" embraces a radical wherein any one or more of an alkyl carbon is substituted with a hydroxyl radical as defined above, for example, monohydroxyalkyl, dihydroxyalkyl and trihydroxyalkyl. More specific examples of hydroxyalkyl include hydroxymethyl, hydroxyethyl and hydroxypropyl.

Hydroxyalkyl may be substituted with, for example, alkyl, hydroxyalkyl, hydroxyalkoxy, hydroxyalkoxyalkyl, amino, aminoalkyl, aryl, aralkyl, and heterocyclyl. Further non-limiting examples include hydroxyalkyl substituted with methyl, isobutyl, benzyl, isopropyl, benzyl and sec-butyl.

The term "hydroxyalkoxy" denotes a hydroxy radical attached to an alkoxy radical.

The term "hydroxyalkoxyalkyl" denotes a hydroxyalkoxy radical attached to an alkyl radical. Non-limiting examples include hydroxyethyl-O-ethyl and hydroxylmethyl-O-ethyl.

Hydroxyalkoxyalkyl may, for example, be substituted with alkyl, hydroxyalkyl, hydroxyalkoxy, hydroxyalkoxyalkyl, amino, aminoalkyl, aryl, aralkyl, and heterocyclyl. Further non-limiting examples include hydroxyalkoxyalkyl substituted with methyl, isobutyl, benzyl, isopropyl and sec-butyl. More specific non-limiting examples of substituted hydroxyalkoxyalkyl include hydroxyethyl-O-ethyl substituted with methyl, isobutyl, benzyl, isopropyl and sec-butyl.

The term "haloalkyl" embraces an alkyl radical wherein any one or more of the alkyl carbon atoms is substituted with halo as defined above. For example, monohaloalkyl, dihaloalkyl and trihaloalkyl. A monohaloalkyl radical, for one example, may have either a bromo, chloro or a fluoro atom within the radical. A dihalo radical may have two of the same halo radicals or a combination of different halo radicals. A trihaloalkyl radical may have three of the same halo radicals or a combination of different halo radicals. Non-limiting examples of haloalkyl include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl, dichloropropyl, iodomethyl, diiodomethyl and triiodomethyl.

The term "alkylene" denotes a linear or branched alkyl radical containing from 2 to about 15 carbon atoms and having two or more attachment points for covalent bonds. The terms "alkylene" and "alkylenyl" may be used interchangeably. Non-limiting examples of alkylene radicals include methylene, ethylene

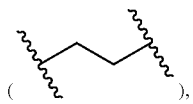

propylene

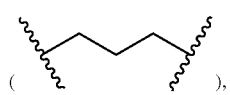

butylene

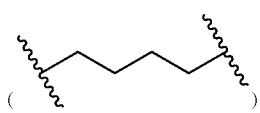 [SMILES: *CCCC*]

and pentylene

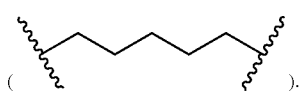 [SMILES: *CCCCC*]

One or more substitutable carbons in an alkylene radical may be replaced with, for example, —CH(R$^4$)—, —CH(R$^4$)—O—, —C(R$^4$)$_2$—,

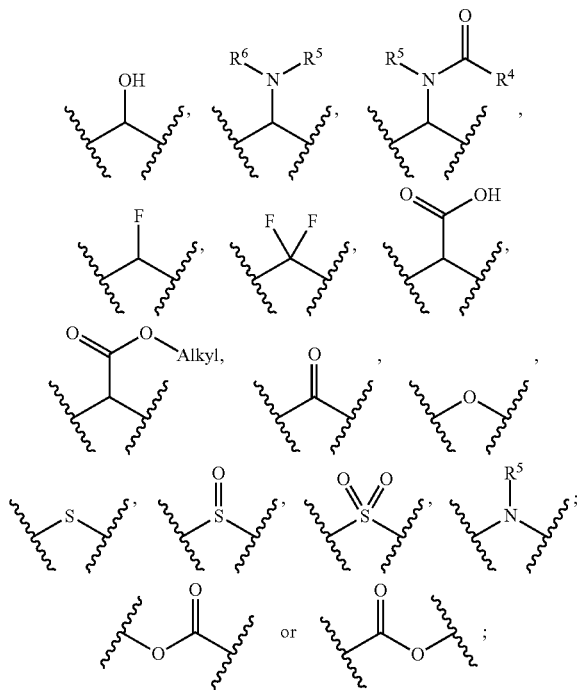

where R$^4$ may be, for example, H, alkyl, acyl, acylamino, amino, aryl, aralkyl, heterocyclyl (e.g., heteroaryl, more specifically phthalimido), alkoxy, alkylthio, alkyl-NH—, or R$^4$ may be taken together with R$^5$ or R$^6$ to form a cyclic ring (e.g., heterocyclyl); R$^5$ may be, for example, H, alkyl, hydroxyalkyl, aryl, heterocyclyl, alkylcarbonyl, arylcarbonyl, heterocyclylcarbonyl, carboxyalkylcarbonyl, alkyloxycarbonylalkylcarbonyl, alkylsulfonyl, arylsulfonyl and heteroarylsulfonyl, or R$^5$ may be taken together with R$^4$ or R$^6$ to form a cyclic ring (e.g., heterocyclyl); and R$^6$ may be, for example, H, alkyl, hydroxyalkyl, aryl, heterocyclyl, alkylcarbonyl, arylcarbonyl, heterocyclylcarbonyl, carboxyalkylcarbonyl, alkyloxycarbonylalkylcarbonyl, alkylsulfonyl, arylsulfonyl and heteroarylsulfonyl, or R$^6$ may be taken together with R$^4$ or R$^5$ to form a cyclic ring (e.g., heterocyclyl).

Examples of substituted alkylene include, ethyleneoxypropylene

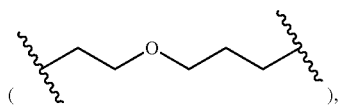

ethyleneoxycarbonylethylene

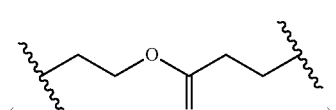

ethyleneoxy

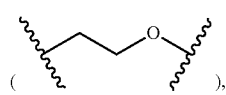

ethyleneoxymethylene

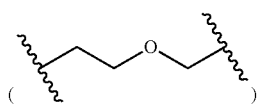

ethyleneoxypropylene

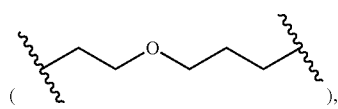 [SMILES: *CCCOCC*]

ethylenecarbonyl

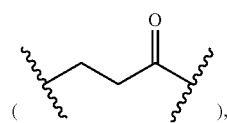

ethylenethiocarbonyl

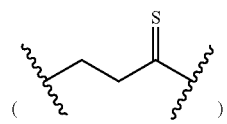 [SMILES: *CCC(*)=S]

and ethylenethionyl

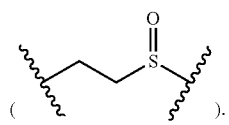

One or more adjacent substitutable carbons in an alkylene radical may be replaced with

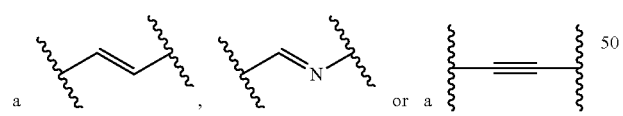

radical.

When one or more substitutable carbons in alkylene are substituted, and the resulting radical has multiple orientations

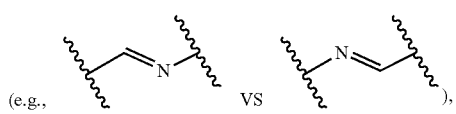

both orientations are embraced by the display of a single orientation.

If two adjacent carbons in an alkylene radical are replaced with heteroatoms, only suitable combinations are embraced. Non-limiting examples of suitable combinations, where two or more adjacent carbon atoms are replaced with O, N or S include

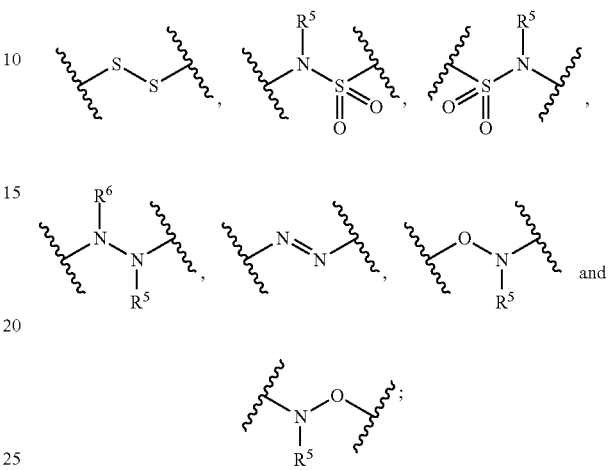

where $R^5$ and $R^6$ are defined as above.

Unsuitable combinations are synthetically unstable combinations and are not embraced by the current invention. Examples of unsuitable combinations include

and geminal heteroatom combinations with

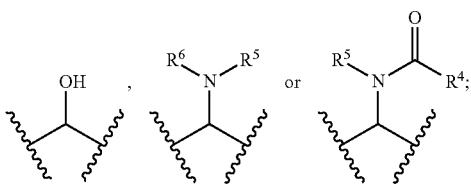

where $R^4$, $R^5$ and $R^6$ are defined as above.

The term "alkoxy" is RO— where R is alkyl as defined above. Non-limiting examples of alkoxy radicals include methoxy, ethoxy and propoxy. The terms "alkyloxy" and "alkoxy" may be used interchangeably.

The term "alkoxyalkyl" refers to an alkoxy moiety substituted with an alkyl radical. Examples of alkoxyalkyl radicals include methoxymethyl, methoxyethyl, methoxypropyl and ethoxyethyl.

The term "alkoxycarbonyl" refers to an alkoxy radical substituted with carbonyl. Non-limiting examples include methoxycarbonyl and ethoxycarbonyl.

The term "alkoxycarbonylalkyl" refers to an alkoxycarbonyl radical substituted with alkyl.

The term "alkyloxycarbonylalkylcarbonyl" refers to alkoxycarbonylalkyl radical substituted with carbonyl (e.g., 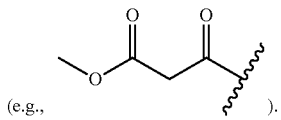 [SMILES: *C(=O)CC(=O)OC]).

The term "alkenyl" refers to an unsaturated, acyclic hydrocarbon radical with at least one double bond. Such alkenyl radicals contain from 2 to about 15 carbon atoms.

The term "alkynyl" refers to an unsaturated, acyclic hydrocarbon radical with at least one triple bond. Such alkynyl radicals containing from 2 to about 15 carbon atoms. A non-limiting example is propargyl.

The term "cyano" denotes a carbon radical having three of four covalent bonds shared by a single nitrogen atom.

The term "carbonyl" denotes a carbon radical having two of four covalent bonds shared with a single oxygen atom.

The term "alkylcarbonyl" denotes an alkyl radical attached to a carbonyl radical.

The term "carbonylalkyl" denotes a carbonyl radical attached to an alkyl radical.

The term "carbonylalkylcarbonyl" denotes a carbonylalkyl radical attached to a carbonyl radical.

The term "thiocarbonyl" denotes a carbon radical having two of four covalent bonds shared with a single sulfur atom.

The term "ureido" denotes

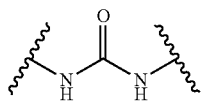

and may be used interchangeably with carbamido.

The term "acyl", is

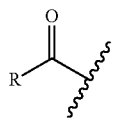

where R may be, for example, H, alkyl, nitrooxyalkyl, aryl and aralkyl. More specific examples of acyl include formyl, acetyl, benzoyl, nitrooxymethylcarbonyl and nitrooxyethylcarbonyl.

The term "acylamino" is

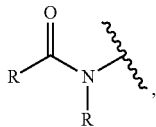

where R may be, for example, H, alkyl, nitrooxyalkyl, aryl and aralkyl. A more specific example of acylamino is acetylamino. The term "carboxy" embraces a hydroxy radical attached to one of two unshared bonds in a carbonyl radical.

The term "carboxyalkyl" embraces a carboxy radical attached to an alkyl radical (e.g., 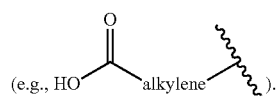).

Non-limiting examples of carboxyalkyl include carboxymethylene and carboxyethylene. The terms "carboxyalkyl" and "hydroxycarbonylalkyl" may be used interchangeably.

The term "carboxyalkylcarbonyl" denotes a carboxyalkyl radical attached to a carbonyl radical.

The term "thiocarboxy" embraces a hydroxyl radical, as defined above, attached to one of two unshared bonds in a thiocarbonyl radical.

The term "thiocarboxyalkyl" embraces a thiocarboxy radical, as defined above, attached to an alkyl radical. Non-limiting examples include thiocarboxymethylene and thiocarboxyethylene.

The term "amido" embraces an amino radical attached to a parent molecular scaffold through carbonyl (e.g., 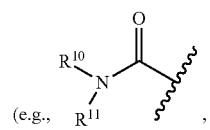, where $R^{10}$ and $R^{11}$ may be, H, alkyl or aralkyl or $R^{10}$ may be taken together with $R^{11}$ to form heterocyclyl, wherein at least one heteroatom is an amido nitrogen). The terms "amido" and "carboxamido" may be used interchangeably. Examples of amido radicals include monoalkylaminocarbonyl, dialkylaminocarbonyl. More specific examples of amido radicals include N-methylamino carbonyl and N,N-dimethylaminocarbonyl.

The term "carbamic" is

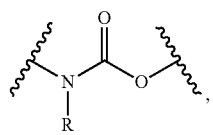, where R may be, for example, H, alkyl or acyl.

The term "cyclic ring" embraces any aromatic or non-aromatic cyclized carbon radical (e.g., aryl and cycloalkyl respectively) which may contain one or more ring heteroatoms (e.g., heteroaryl and heterocyclyl).

The term "cycloalkyl" embraces any monocyclic, bicyclic or tricyclic cyclized carbon radical of 3 to about 15 carbon atoms that is fully or partially saturated. Cycloalkyl may be attached to an aryl, cycloalkyl or a heterocyclyl radical in a fused or pendant manner.

Cycloalkyl may be substituted with alkyl, alkoxy, carboxyalkyl, hydroxyalkyl, amino, acylamino, amido, alkylamino, nitrooxyalkyl, nitrooxy, carbonyl, acyl, aralkyl, aryl, heterocyclyl or cycloalkyl.

The term "aryl" refers to any monocyclic, bicyclic or tricyclic cyclized carbon radical, wherein at least one ring is aromatic. An aromatic radical may be attached to a non-aromatic cycloalkyl or heterocyclyl radical in a fused or pendant manner. Examples of aryl radicals include, but are not limited to, phenyl and naphthyl.

The term "arylcarbonyl" denotes an aryl radical attachable through a carbonyl radical to the scaffold of Formula I or II. The terms "aroyl" and "arylcarbonyl" may be used interchangeably. Examples of arylcarbonyl include benzoyl and toluoyl.

The term "aralkyl" embraces aryl attachable through an alkylene radical to the scaffold of Formula I or II and may be used interchangeably with "arylalkyl". Examples of aralkyl include benzyl, diphenylmethyl, triphenylmethyl, phenylethyl and diphenylethyl. The terms "benzyl" and "phenylmethyl" may be used interchangeably.

The term "heterocyclyl" refers to any monocyclic, bicyclic or tricyclic ring system having from 5 to about 15 ring members selected from carbon, nitrogen, sulfur and oxygen, wherein at least one ring member is a heteroatom. Heterocyclyl embraces a fully saturated, partially saturated and fully unsaturated radical (e.g., heteroaryl). Heterocyclyl may be fused or attached in a pendant manner to another heterocyclyl, aryl or cycloalkyl radical.

Heterocyclyl embraces combinations of different heteroatoms within the same cyclized ring system. When nitrogen is a ring member, heterocyclyl may be attached to the parent molecular scaffold through a ring nitrogen. Non-limiting examples of fully saturated five and six-membered heterocyclyl include: pyrrolidinyl, imidazolidinyl, piperidinyl, piperazinyl, tetrahydrofuranyl, morpholinyl and thiazolidinyl. Examples of partially saturated heterocyclyl include dihydrothiophenyl

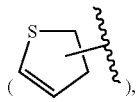

dihydropyranyl, dihydrofuranyl and dihydrothiazolyl.

Heterocyclyl may be substituted, for example, with alkyl, alkoxy, carboxyalkyl, hydroxyalkyl, amino, acylamino, amido, alkylamino, nitrooxyalkyl, nitrooxy, carbonyl, acyl, aralkyl, aryl, heterocyclyl or cycloalkyl. Non-limiting examples include, five-membered heterocyclyl substituted with hydroxyalkyl, alkoxyalkyl, acyl, carbonyl or alkylaminocarbonyl. More specifically, pyrrolidinyl may be substituted with hydroxyalkyl, alkoxyalkyl, acyl, carbonyl or alkylaminocarbonyl. Substituted and un-substituted 5-membered heterocyclyl may be fused or attached in a pendant manner to an additional heterocyclyl, aryl or cycloalkyl radical. For example, pyrrolidinyl-2,5-dione may be fused to phenyl giving isoindolinyl, 1,3-dione (also termed "phthalimido").

The term "heterocycloalkyl" embraces a heterocyclyl radical attached to the parent molecular scaffold through an alkyl radical (e.g., heterocyclyl-alkyl-scaffold).

Six-membered heterocyclyl may be substituted with, for example, hydroxyalkyl, alkoxyalkyl, acyl, carbonyl or alkylaminocarbonyl. More specifically, piperidinyl, piperazinyl and morpholinyl may be substituted with hydroxyalkyl, alkoxyalkyl, acyl, carbonyl or alkylaminocarbonyl. Substituted and un-substituted 6-membered heterocyclyl may be fused or attached in a pendant manner to an additional heterocyclyl, aryl or cycloalkyl radical.

The term "heteroaryl" refers to an aromatic heterocyclyl radical. Heteroaryl may be fused or attached in a pendant manner to another heterocyclyl, aryl or cycloalkyl radical. Heteroaryl embraces combinations of different heteroatoms within the same cyclized radical. When nitrogen is a ring member, heteroaryl may be attached to the parent molecular scaffold through a ring nitrogen. Non-limiting examples of heteroaryl include pyridyl, thienyl, furanyl, pyrimidyl, imidazolyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, benzothienyl, indolyl, benzothiazolyl, benzooxazolyl, benzimidazolyl, isoindolyl, benzotriazolyl

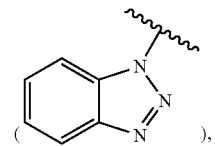

purinyl and thianaphthenyl. The term "heteroaryl" is also understood to include the N-oxide derivative of any nitrogen containing heteroaryl.

The term "heteroaryloxy" embraces a heteroaryl radical attached through an oxygen atom to the parent molecular scaffold (e.g., heteroaryl-O-scaffold).

The term "alkylamino" embraces an alkyl radical attached to a molecular scaffold through an amino radical (e.g., alkyl-NH-scaffold). Specific non-limiting examples of alkylamino include N,N-dimethylamino-scaffold and N-methylamino-scaffold.

The term "aminoalkyl" embraces an amino radical attached to a molecular scaffold through an alkyl radical (e.g., $NH_2$-alkyl-scaffold).

The term "aralkoxy" embraces an arylalkyl radical attached through an oxygen atom to the parent molecular scaffold. The terms "arylalkoxy" and "aralkoxy" may be used interchangeably.

The term "aryloxy" is RO—, where R is aryl.

The term "arylthio" is RS—, where R is aryl.

The term "alkylthio" is RS—, where R is alkyl (e.g., alkyl-S-scaffold).

The term "thiolalkyl" is HSR—, where R is alkyl (e.g., HS-alkyl-scaffold).

The term "aryloxyalkyl" embraces an aryloxy radical attached to an alkyl radical.

The term "sulfonyl" is —$SO_2$—.

The term "alkylsulfonyl" embraces an alkyl radical attached to a sulfonyl radical, where alkyl is defined as above.

The term "arylsulfonyl" embraces an aryl radical attached to a sulfonyl radical.

The term "heteroarylsulfonyl" embraces a heteroaryl radical attached to a sulfonyl radical.

The term "alkylsulfonylalkyl", embraces an alkylsulfonyl radical attached to an alkyl radical, where alkyl is defined as above.

The term "haloalkylsulfonyl" embraces a haloalkyl radical attached to a sulfonyl radical, where haloalkyl is defined as above.

The term "sulfonamide" denotes sulfonyl attached to an amino radical. For example: $NH_2SO_2$— and —$NHSO_2$—. Sulfonamide may be used interchangeably with sulfamyl, sulfonamido and aminosulfonyl.

The term "guanidino" denotes

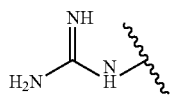

and may be used interchangeably with guanido.

The term "imine" denotes a compound containing the structure >C=N—.

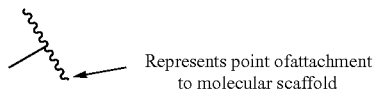
Represents point of attachment to molecular scaffold

The term "coxib" characterizes any member of a class of nonsteroidal anti-inflammatory drugs that causes fewer gastrointestinal side effects by selective inhibition of prostaglandin formation. The terms "coxib" and "selective COX-2 inhibitor" may be used interchangeably.

The term "pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

The term "pharmaceutically-acceptable salt" refers to a salt which may enhance desired pharmacological activity or may enhance stability of a compound. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, hydriodic acid, sulfuric acid, nitric acid and phosphoric acid. Examples of acid addition salts formed with organic acids include acetic acid, propionic acid, hexanoic acid, heptanoic acid, cyclopentanepropionic acid, glycolic acid, pyruvic acid, lactic acid, citric acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, glucoheptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxynaphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases (e.g., cytosine, thymine, uracil and guanine).

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "solvate" denotes a molecular or ionic complex of molecules or ions of solvent with those of a compound of the present invention. The term "solvate" embraces the term "hydrate".

The term "hydrate" denotes a compound of the present invention containing water combined in the molecular form.

Some of the compounds described contain one or more stereocenters and are meant to include R, S and mixtures of R and S forms for each stereocenter present.

The term "NO-releasing" means releasing, liberating or generating nitric oxide (NO).

LIST OF ABBREVIATIONS

ACN acetonitrile
Boc tert-butyloxycarbonyl
DCI dicyclohexylcarbodiimide
DCM dichloromethane or methylenechloride
DIPEA diisopropylethylamine
DMAP 4-dimethylaminopyridine or N,N-dimethylaminopyridine
DME 1,2-dimethoxyethane
DMF N,N-dimethylformamide
DMSO dimethylsulfoxide
eq. equivalents
EtOAC ethyl acetate
EtOH ethanol
Fmoc fluorenylmethyloxycarbonyl chloride
HPLC high performance liquid chromatography
hr hour
hrs hours
$K_2CO_3$ potassium carbonate
LC/MS liquid chromatography mass spectrometry
LC/MS/MS liquid chromatography tandem mass spectrometry
MeOH methanol
$MgSO_4$ magnesium sulfate
min. minute(s)
mL milliliter
mmol millimole
$Na_2S_2O_3$ sodium thiosulfate
$Na_2SO_4$ sodium sulfate
NaH sodium hydride
$NaHCO_3$ sodium bicarbonate
NaI sodium Iodide
$NaIO_4$ sodium periodate
$NaOCH_3$ sodium methoxide
NBS N-bromosuccinimide
NIS N-iodosuccinimide
NMR nuclear magnetic resonance
NO nitric oxide
Psi pounds per square inch
PyBOP benzotriazole-1-yl-oxy-tris-(dimethylamino)-phosphonium hexafluorophosphate
$RuCl_3$ ruthenium trichloride hydrate
TEA triethylamine
TFA trifluoroacetic acid
THF tetrahydrofuran
TLC thin layer chromatography
TSA p-toluenesulfonic acid

TABLE 4

Additional Suitable Protecting Groups

Acetyl (Ac)
Acylals
Benzoyl (Bz)
Benzyl (Bn, Bnl)
Benzyl esters
Carbamate
Carbobenzyloxy (Cbz)

TABLE 4-continued

Additional Suitable Protecting Groups

Dimethoxytrityl, [bis-(4-methoxyphenyl)phenylmethyl] (DMT)
Dithianes
Ethoxyethyl ethers (EE)
Methoxymethyl ether (MOM)
Methoxytrityl [(4-methoxyphenyl)diphenylmethyl], MMT)
Methyl Ethers
Methyl (Me)
Methyl esters
Methylthiomethyl ether
Orthoesters
Oxazoline
Pivaloyl (Piv)
Phthalimido
p-Methoxybenzyl carbonyl (Moz or MeOZ)
p-Methoxybenzyl (PMB)
Propargyl alcohols
Silyl groups (e.g., trimethylsilyl (TMS), tert-butyldimethylsilyl (TBDMS), tri-iso-propylsilyloxymethyl (TOM) and triisopropylsilyl (TIPS))
Silyl esters
tert-Butyl esters
tert-Butyloxycarbonyl (BOC or tBOC)
Tetrahydropyranyl (THP)
Tosyl (Ts or Tos)
Trimethylsilylethoxymethyl (SEM)
Trityl (triphenylmethyl, Tr)
β-Methoxyethoxymethyl ether (MEM)
(4-nitrophenyl)sulfonyl or (4-nitrophenyl)(dioxido)-lambda(6)-sulfanyl) (Nosyl)
2-cyanoethyl
2-nitrophenylsulfenyl (Nps)
3,4-Dimethoxybenzyl (DMPM)
9-Fluorenylmethyloxycarbonyl (FMOC)
2,2,4,6,7-Pentamethyldihydrobenzofuran-5-sulfonyl (Pbf)

TABLE 5

Amino Acids

| No. | Amino Acid | CAS# |
|---|---|---|
| A1 | N-alpha-Carbobenzyloxy-L-ornithine | [2640-58-6] |
| A2 | N-alpha-Ac-L-ornithine | Synthesized from N-delta-Boc-L-ornithine with acetic anhydride in pyridine, and followed by removal of the Boc protecting group. |
| A3 | 3-Aminopropanoic acid | [107-95-9] |
| A4 | 4-Aminobutyric acid | [56-12-2] |
| A5 | 5-Aminovaleric acid | [660-88-8] |

C. General Synthetic Schemes

Compounds of the present invention can be prepared using methods illustrated in general synthetic schemes and experimental procedures detailed below. These general synthetic schemes and experimental procedures are presented for purposes of illustration and are not intended to be limiting. Starting materials used to prepare compounds of the present invention are commercially available or can be prepared using routine methods known in the art.

Step 1: Celecoxib was made by previously published procedures (Penning, et. al. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (Celecoxib). *J. Med. Chem.* 1997, 40, 1347-1365. Celecoxib (5.0 g, 13.11 mmol) was dissolved in 120 mL ethanol, then 40 mL of water was added. Aqueous sodium hydroxide (0.49 M NaOH, 29.83 mL, 13.11 mmol) was added and stirred at room temperature for 5 minutes. The product was azeotroped with 25 mL acetonitrile and 25 mL ethanol. The resulting sodium salt of celecoxib (2a) was dried under vacuum to yield a white solid (5.32 g, quantitative yield). Comparing starting material to product by thin layer chromatography confirmed the formation of the desired sodium salt.

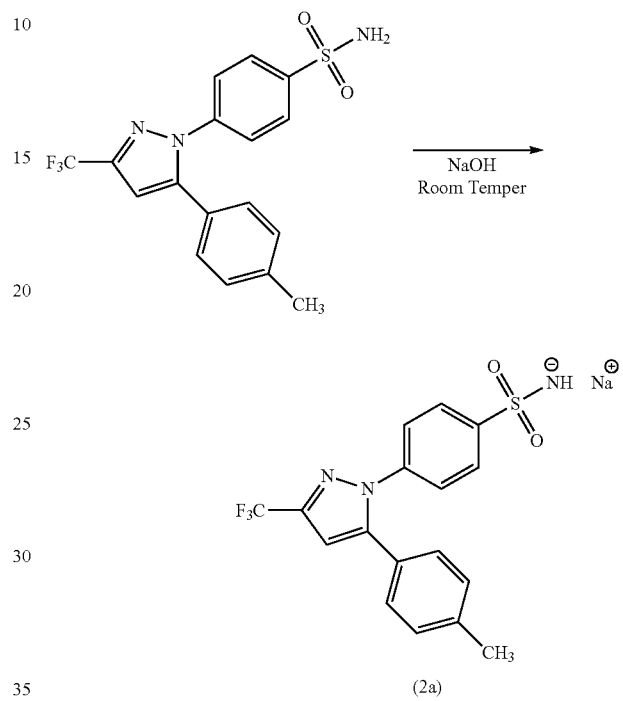

(2a)

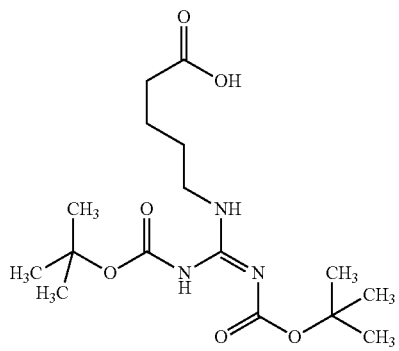

Step 2: Guanidine formation is done by reaction amines with guanylating agents. 5-Amino valeric acid (A5) (0.093 g, 0.791 mmol) and N,N-Bis(Boc)-1H-pyrazole-1-carboxamide (0.270 g, 0.870 mmol) were suspended in pyridine (2.0 mL) and stirred at 25° C. for 2 days. The homogenous reaction was treated with 1N NaOH and extracted into ethyl acetate. The aqueous layer was acidified (pH 3) with 1N HCl and then extracted into ethyl acetate. The combined organics were washed with brine, dried over $Na_2SO_4$, filtered and concentrated under reduced pressure to provide (B5) as a white solid (0.259 g, 91%). LC $t_r$=4.20 minutes (C-18 column, 5 to 95% acetonitrile/water over 6 minutes at 1.7 ml/min with detection 254 nm, at 23° C.). Protected guanidine compounds of the amino acid starting materials A1-A4 (Table 5) can all be made using this method.

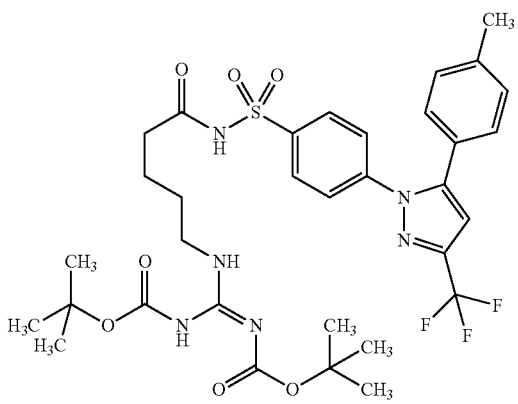 [SMILES: Cc1ccc(-c2cc(C(F)(F)F)nn2-c2ccc(S(=O)(=O)NC(=O)CCCCN/C(=N/C(=O)OC(C)(C)C)NC(=O)OC(C)(C)C)cc2)cc1]

Step 3: Acid coupling to sulfonamide: Protected guanidine (B5) (0.250 g, 0.696 mmol) and benzotriazole-1-yl-oxy-tris-(dimethylamino)-phosphonium hexafluorophosphate (PyBOP) (306 mg, 0.59 mmol) were added to a suspension of compound (2a) (0.617 g, 1.53 mmol) in methylene chloride (2.0 mL). The resulting mixture was stirred at 25° C. overnight. The methylene chloride was removed under reduced pressure and the residue was taken up in ethyl acetate. The organic layer was washed with water, brine, dried over magnesium sulfate filtered and concentrated under reduced pressure. The product was chromatographed to yield the product (C5) as a residue (0.288 g, 57% yield). LC $t_r$=4.20 minutes (C-18 column, 5 to 95% acetonitrile/water over 6 minutes at 1.7 ml/min with detection 254 nm, at 23° C.). ES (pos) MS m/z 723 (M+H calcd for $C_{33}H_{41}N_6SO_7F_3$ requires 723).

Step 4: Boc-Deprotection is accomplished by standard condition using neat trifluoroacetic acid, mixtures of trifluoroacetic acid (TFA) with methylene chloride, or hydrochloride acid (HCl) in dioxane. Compound C5 (0.288 g, 0.398 mmol) was treated with 4N HCl/dioxane (0.219 mL, 0.876 mmol). The mixture was stirred at 25° C. overnight. Additional 4N HCl/dioxane (0.099 mL, 0.398 mmol) was added and continued stifling at 25° C. overnight. Additional 4N HCl/dioxane (0.219 mL, 0.876 mmol) was added and stifling was continued for 2 days. Additional 4N HCl/dioxane (0.219 mL, 0.876 mmol) was added and stirring was continued for 2 days. Again, additional 4N HCl/dioxane (0.219 mL, 0.876 mmol) was added and stirring was continued over the weekend. The reaction mixture was concentrated under reduced pressure and then subjected to reverse phase chromatography (acetonitrile/water with 0.05% trifluoroacetic acid) to obtain compound 4 as a white foam (56 mg, 25%). ¹H NMR (400 MHz, DMSO-$d_6$) δ 12.25 (s, 1H), 7.98 (d, J=8.4 Hz, 2H), 7.60 (d, J=8.8 Hz, 2H), 7.46 (t, J=5.6 Hz, 2H), 7.25-7.20 (m, 4H), 7.17-6.60 (br s, 1H), 4.00-3.20 (br s, 3H), 3.09-2.98 (m, 2H), 2.32 (s, 3H), 2.27 (t, J=6.7 Hz, 2H), 1.49-1.32 (m, 4H). LC $t_r$=3.80 minutes (C-18 column, 5 to 95% acetonitrile/water over 6 minutes at 1.7 ml/min with detection 254 nm, at 23° C.). ES (pos) MS m/z 523 (M+H calcd for $C_{23}H_{25}N_6SO_3F_3$ requires 523).

D. Species Compounds Preparations of Tables 2 and 3

Example 5

(S)-2-Amino-5-guanidino-N-((4-(5-(p-tolyl)-3-(trifluoromethyl)-1H-pyrazol-1-yl)phenyl)sulfonyl)pentanamide

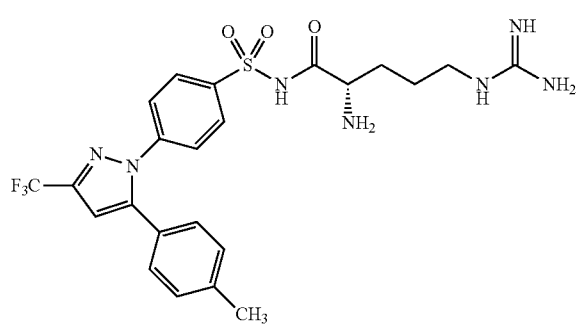 [SMILES: Cc1ccc(-c2cc(C(F)(F)F)nn2-c2ccc(S(=O)(=O)NC(=O)[C@@H](N)CCCNC(=N)N)cc2)cc1]

Step 1: Celecoxib was made by previously published procedures (Penning, et. al. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (Celecoxib). *J. Med. Chem.* 1997, 40, 1347-1365). Celecoxib (5.0 g, 13.11 mmol) was dissolved in 120 mL ethanol, then 40 mL of water was added. Aqueous sodium hydroxide (0.49 M NaOH, 29.83 mL, 13.11 mmol) was added and stirred at room temperature for 5 minutes. The product was azeotroped with 25 mL acetonitrile and 25 mL ethanol. The resulting sodium salt of celecoxib (2a) was dried under vacuum to yield a white solid (5.32 g, quantitative yield). Comparing starting material to product by thin layer chromatography confirmed the formation of the desired sodium salt.

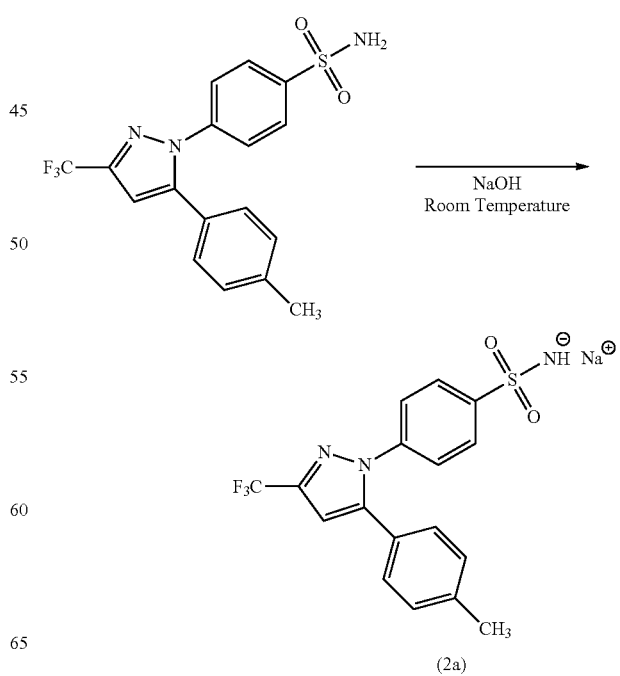

(2a)

Step 2: (S)-2-(tert-Butoxycarbonylamino)-5-(3-(2,2,4,6,7-pentamethyl-2,3-dihydrobenzofuran-5-ylsulfonyl)guanidino)pentanoic acid (Boc-L-Arg(Pbf)-OH) (0.126 g, 0.240 mmol) and benzotriazole-1-yl-oxy-tris-(dimethylamino)-phosphonium hexafluorophosphate (PyBOP) (0.125 g, 0.240 mmol) were added to a suspension of the compound (2) (0.194 g, 0.480 mmol) in methylene chloride (2.0 mL). The resulting mixture was stirred at 25° C. for 45 min and then Hz, 2H), 7.11 (d, J=8.2 Hz, 2H), 6.74 (s, 1H), 6.34-6.20 (br m, 2H), 5.55-5.42 (br m, 1H), 4.33-4.22 (br m, 1H), 3.31-3.18 (br m, 2H), 2.98 (s, 2H), 2.58 (s, 3H), 2.52 (s, 3H), 2.38 (s, 3H), 2.10 (s, 3H), 1.47 (s, 6H), 1.39 (br s, 9H), 1.31-1.24 (m, 4H). LC $t_r$=5.25 minutes (C-18 column, 5 to 95% acetonitrile/water over 6 minutes at 1.7 ml/min with detection 254 nm, at 23° C.).

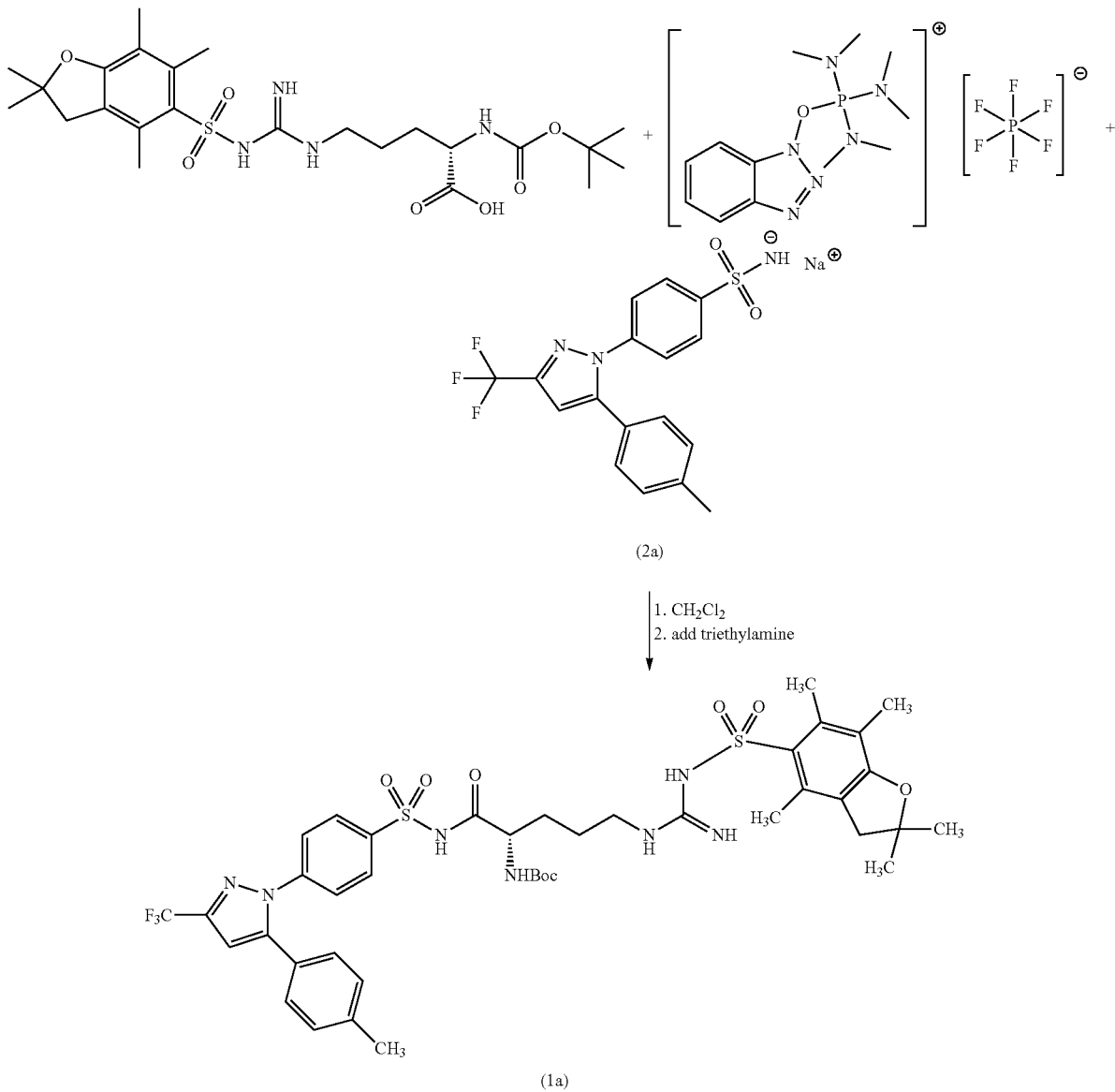

triethylamine (0.152 mL, 1.09 mmol) was added and the mixture was stirred at 25° C. for 4 h. Additional triethylamine (0.152 mL, 1.09 mmol) was added and the mixture was stirred at 25° C. for 2 days. The methylene chloride was removed under reduced pressure and the residue was taken up in ethyl acetate. The organic layer was washed with 1N HCl, brine, dried over Na$_2$SO$_4$, filtered and concentrated under reduced pressure. The residue was chromatographed using ethyl acetate and hexanes to provide compound (1a) as a white foam (162 mg, 76% yield). $^1$H NMR (400 MHz, CDCl$_3$) δ 8.03 (d, J=8.4 Hz, 2H), 7.45 (d, J=8.7 Hz, 2H), 7.18 (d, J=8.00

Step 3: Compound (1a) (0.160 g, 0.180 mmol) was treated with 95% trifluoroacetic acid in methylene chloride (1.5 mL). The mixture was stirred at 25° C. for 1 h and then concentrated under reduced pressure. The residue was purified by reverse phase chromatography (acetonitrile/water with 0.05% trifluoroacetic acid) to provide the title compound (3) as a tan foam (44 mg, 32% yield). $^1$H NMR (400 MHz, DMSO-d$_6$) δ 7.89 (d, J=8.4 Hz, 2H), 7.60-7.52 (br m, 1H), 7.45 (d, J=8.4 Hz, 2H), 7.21 (d, J=3.9 Hz, 2H), 7.20 (d, J=2.5 Hz, 2H), 5.00-4.00 (br m, 6H), 3.54-3.47 (br m, 1H), 3.14-3.03 (br m, 2H), 2.98 (s, 2H), 1.80-1.68 (m, 1H), 1.67-1.58

(m, 1H), 1.57-1.40 (m, 2H). LC t$_r$=3.20 minutes (C-18 column, 5 to 95% acetonitrile/water over 6 minutes at 1.7 ml/min with detection 254 nm, at 23° C.). ES (pos) MS m/z 538 (M+H calcd for C$_{23}$H$_{26}$N$_7$SO$_3$F$_3$ requires 538).

(H-L-Arg(Pbf)-OH) (1.0 eq.) is dissolved in pyridine (0.25 M) and acetic anhydride (1.2 eq.) is added to acylate the primary amine, after 1 h the reaction is quenched with aqueous acid, extracted with ethyl acetate, and purified by chro-

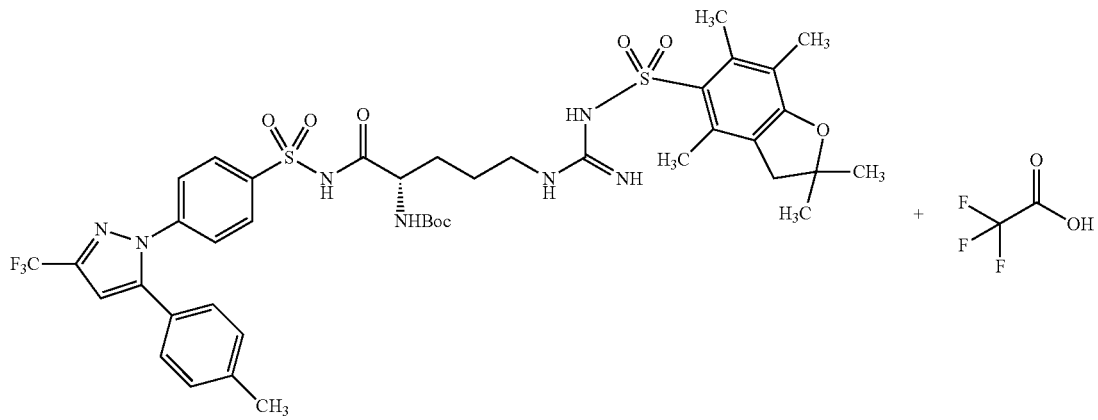

(1a)

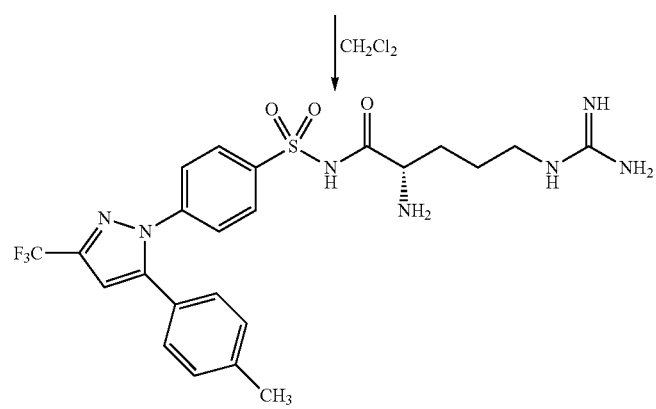

(3)

Example 6

(S)-2-Acetamido-5-guanidino-N-((4-(5-(p-tolyl)-3-(trifluoromethyl)-1H-pyrazol-1-yl)phenyl)sulfonyl) pentanamide matography to afford (S)-2-acetamido-5-(3-((2,2,4,6,7-pentamethyl-2,3-dihydrobenzofuran-5-yl)sulfonyl) guanidino) pentanoic acid (Ac-L-Arg(Pbf)-OH).

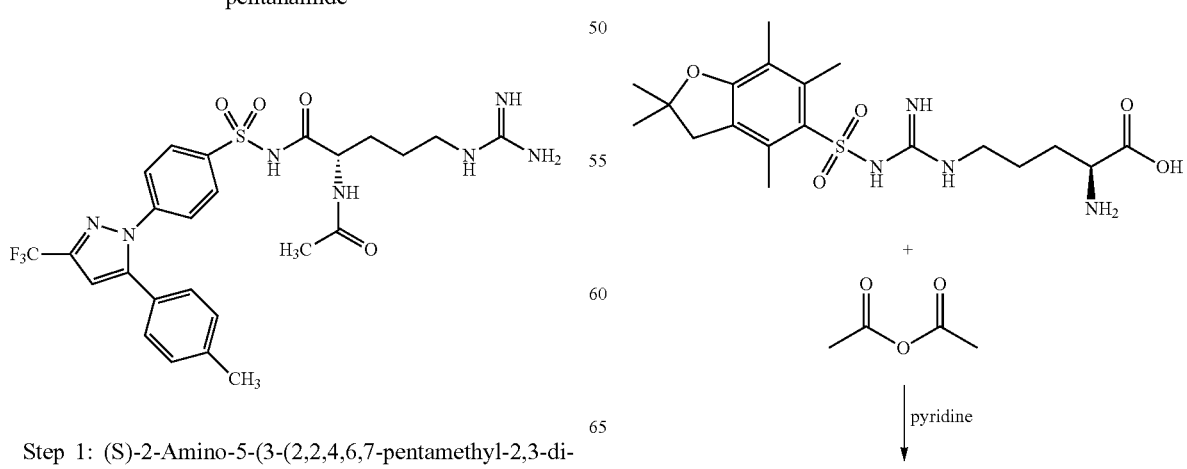

Step 1: (S)-2-Amino-5-(3-(2,2,4,6,7-pentamethyl-2,3-dihydrobenzofuran-5-ylsulfonyl) guanidino)pentanoic acid -continued

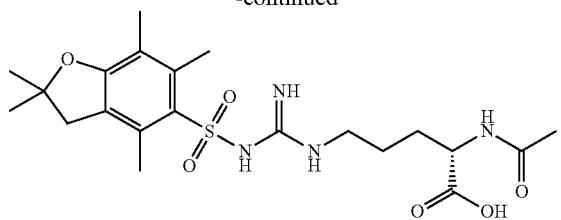

Step 2: Using the methods of Example 5, Steps 2 and 3, with substitution of (S)-2-acetamido-5-(3-((2,2,4,6,7-pentamethyl-2,3-dihydrobenzofuran-5-yl)sulfonyl)guanidino) pentanoic acid (Ac-L-Arg(Pbf)-OH) for the Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 7

(S)-2-Formamido-5-guanidino-N-((4-(5-(p-tolyl)-3-(trifluoromethyl)-1H-pyrazol-1-yl)phenyl)sulfonyl) pentanamide

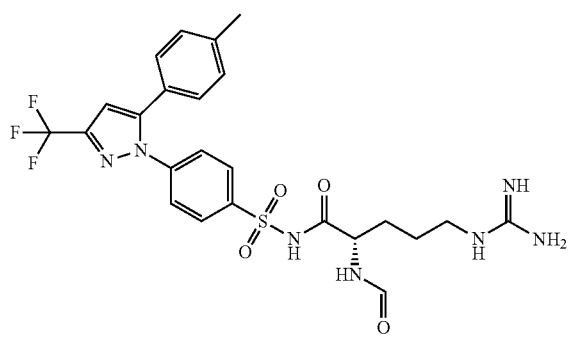 [SMILES: Cc1ccc(-c2cc(C(F)(F)F)nn2-c2ccc(S(=O)(=O)NC(=O)[C@H](CCCNC(=N)N)NC=O)cc2)cc1]

Using the methods of Example 6, Step 1, with substitution of formic anhydride as the acylating agent rather than acetic anhydride and using the methods of Example 5, Steps 2 and 3, with substitution of the product of the previous reaction for Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 8

(S)-5-Guanidino-2-propionamido-N-((4-(5-(p-tolyl)-3-(trifluoromethyl)-1H-pyrazol-1-yl)phenyl)sulfonyl)pentanamide

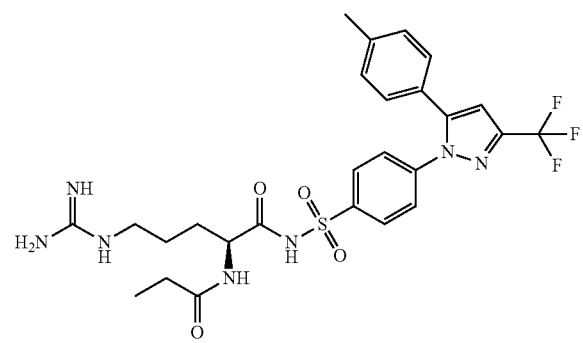 [SMILES: CCC(=O)N[C@@H](CCCNC(=N)N)C(=O)NS(=O)(=O)c1ccc(-n2nc(C(F)(F)F)cc2-c2ccc(C)cc2)cc1]

Using the methods of Example 6, Step 1, with substitution of propionic anhydride as the acylating agent rather than acetic anhydride and using the methods of Example 5, Steps 2 and 3, with substitution of the product of the previous reaction for Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 9

(S)—N-(5-Guanidino-1-oxo-1-(4-(5-(p-tolyl)-3-(trifluoromethyl)-1H-pyrazol-1-yl)phenylsulfonamido)pentan-2-yl)benzamide

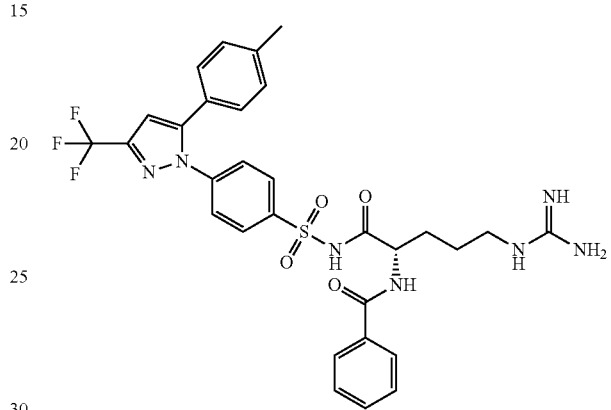

Using the methods of Example 6, Step 1, with substitution of benzoic anhydride as the acylating agent rather than acetic anhydride and using the methods of Example 5, Steps 2 and 3, with substitution of the product of the previous reaction for Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 10

(S)-2-Amino-6-guanidino-N-((4-(5-(p-tolyl)-3-(trifluoromethyl)-1H-pyrazol-1-yl)phenyl)sulfonyl)hexanamide

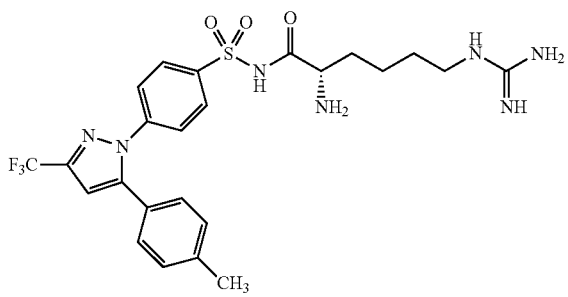 [SMILES: Cc1ccc(-c2cc(C(F)(F)F)nn2-c2ccc(S(=O)(=O)NC(=O)[C@@H](N)CCCCNC(=N)N)cc2)cc1]

Using the methods of Example 5, Steps 2 and 3, with substitution of (S)-2-(((9H-Fluoren-9-yl)methoxy)carbonylamino)-6-(3-(2,2,4,6,7-pentamethyl-2,3-dihydrobenzofuran-5-ylsulfonyl) guanidino)hexanoic acid (Fmoc-L-HomoArg(Pbf)-OH) for the Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 11

(S)-2-Acetamido-6-guanidino-N-((4-(5-(p-tolyl)-3-(trifluoromethyl)-1H-pyrazol-1-yl)phenyl)sulfonyl)hexanamide

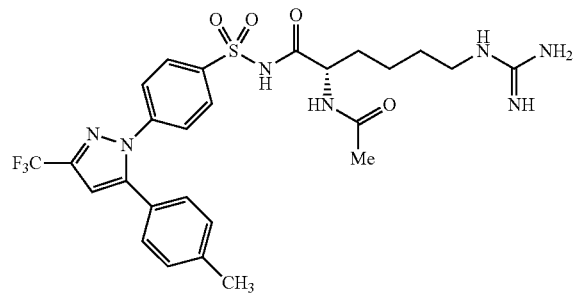 [SMILES: CC(=O)N[C@@H](CCCCNC(=N)N)C(=O)NS(=O)(=O)c1ccc(-n2nc(C(F)(F)F)cc2-c2ccc(C)cc2)cc1]

Step 1: (S)-2-(((9H-Fluoren-9-yl)methoxy)carbonylamino)-6-(3-(2,2,4,6,7-pentamethyl-2,3-dihydrobenzofuran-5-ylsulfonyl)guanidino)hexanoic acid (Fmoc-L-HomoArg(Pbf)-OH) is treated with 20-50% piperidine in N,N-dimethylformamide (0.1 M). After 10 min the reaction is concentrated and the residue is purified using reverse phase chromatography (acetonitrile/water with 0.05% trifluoroacetic acid) to provide the free primary amine. This amine (1.0 eq.) is dissolved in pyridine (0.25 M) and acetic anhydride (1.2 eq.) is added to acylate the primary amine, after 1 h the reaction is quenched with aqueous acid, extracted with ethyl acetate, and purified by chromatography to afford (S)-2-acetamido-6-(3-((2,2,4,6,7-pentamethyl-2,3-dihydrobenzofuran-5-yl)sulfonyl)guanidino)hexanoic acid (Ac-L-HomoArg(Pbf)-OH).

Step 2: Using the methods of Example 5, Steps 2 and 3, with substitution of (S)-2-acetamido-6-(3-((2,2,4,6,7-pentamethyl-2,3-dihydrobenzofuran-5-yl)sulfonyl)guanidino)hexanoic acid (Ac-L-HomoArg(Pbf)-OH) for the Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 12

(S)-2-Formamido-6-guanidino-N-((4-(5-(p-tolyl)-3-(trifluoromethyl)-1H-pyrazol-1-yl)phenyl)sulfonyl)hexanamide

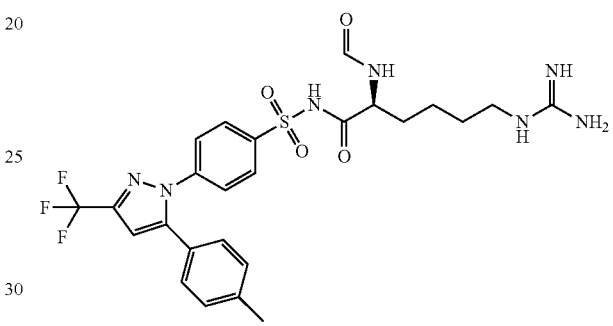

Using the methods of Example 11, Step 1, with substitution of formic anhydride as the acylating agent rather than acetic anhydride and using the methods of Example 5, Steps 2 and 3, with substitution of the product of the previous reaction for Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

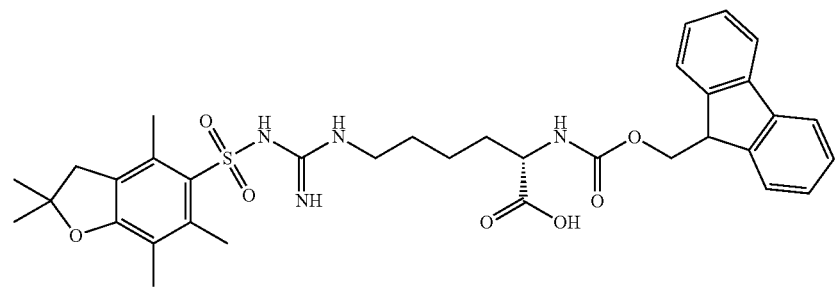

1. 20-50% piperidine in DMF (removal of protecting group)
2. pyridine (0.25M) and acetic anhydride (acylation of the amine)

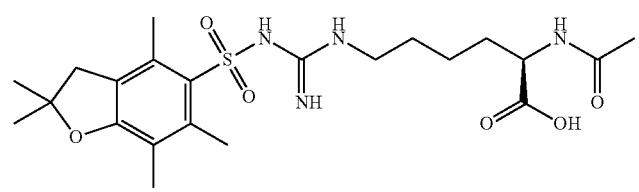

Example 13

(S)-6-Guanidino-2-propionamido-N-((4-(5-(p-tolyl)-3-(trifluoromethyl)-1H-pyrazol-1-yl)phenyl)sulfonyl)hexanamide

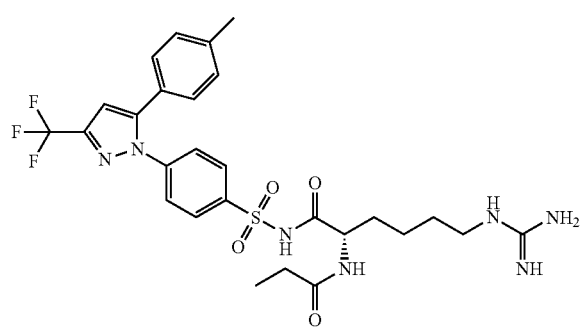 [SMILES: CCC(=O)N[C@@H](CCCCNC(=N)N)C(=O)NS(=O)(=O)c1ccc(-n2nc(C(F)(F)F)cc2-c2ccc(C)cc2)cc1]

Using the methods of Example 11, Step 1, with substitution of propionic anhydride as the acylating agent rather than acetic anhydride and using the methods of Example 5, Steps 2 and 3, with substitution of the product of the previous reaction for Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 14

(S)—N-(6-Guanidino-1-oxo-1-(4-(5-(p-tolyl)-3-(trifluoromethyl)-1H-pyrazol-1-yl)phenylsulfonamido)hexan-2-yl)benzamide

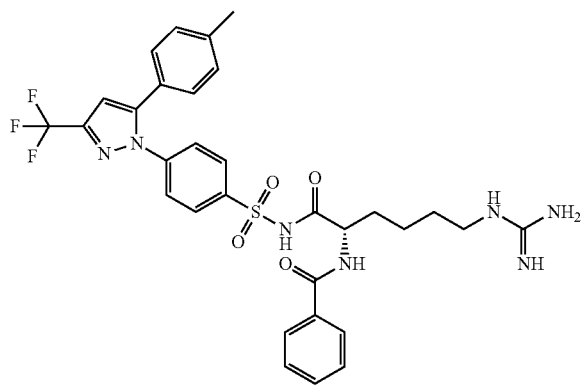 [SMILES: Cc1ccc(-c2cc(C(F)(F)F)nn2-c2ccc(S(=O)(=O)NC(=O)[C@H](CCCCNC(=N)N)NC(=O)c3ccccc3)cc2)cc1]

Using the methods of Example 11, Step 1, with substitution of benzoic anhydride as the acylating agent rather than acetic anhydride and using the methods of Example 5, Steps 2 and 3, with substitution of the product of the previous reaction for Example 5 reagent (S)-2-(tert-Butoxycarbonylamino)-5-(3-(2,2,4,6,7-pentamethyl-2,3-dihydrobenzofuran-5-ylsulfonyl) guanidino)pentanoic acid (Boc-L-Arg(Pbf)-OH), the title compound is afforded.

Example 15

(S)-2-Amino-5-(2-hydroxyguanidino)-N-((4-(5-(p-tolyl)-3-(trifluoromethyl)-1H-pyrazol-1-yl)phenyl)sulfonyl)pentanamide

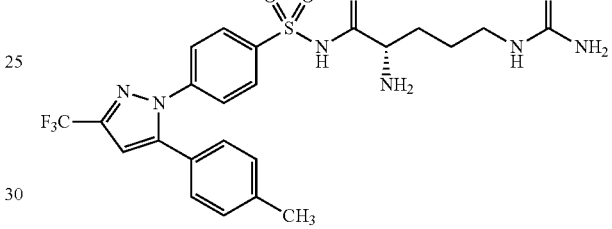

Step 1: (S)-2-((((9H-Fluoren-9-yl)methoxy)carbonyl)amino)-5-(3-(tert-butoxy)-2-((2,2,4,6,7-pentamethyl-2,3-dihydrobenzofuran-5-yl)sulfonyl)guanidino)pentanoic acid (Fmoc-L-Arg(tBuO)(Pbf)-OH) can be made as described in "Preparation of NG-Substituted L-Arginine Analogues Suitable for Solid Phase Peptide Synthesis" Martin et. al; *J. Org. Chem.*, 2008, 73 (19), pp. 7849-7851. Using the methods of Example 5, Step 2, with substitution of (Fmoc-L-Arg(tBuO)(Pbf)-OH) for Example 5 reagent (S)-2-(tert-Butoxycarbonylamino)-5-(3-(2,2,4,6,7-pentamethyl-2,3-dihydrobenzofuran-5-ylsulfonyl)guanidino)pentanoic acid (Boc-L-Arg(Pbf)-OH) (1.25 eq.) the intermediate compound (S)-(9H-Fluoren-9-yl)methyl (5-(3-(tert-butoxy)-2-((2,2,4,6,7-pentamethyl-2,3-dihydrobenzofuran-5-yl)sulfonyl)guanidino)-1-oxo-1-(4-(5-(p-tolyl)-3-(trifluoromethyl)-1H-pyrazol-1-yl)phenylsulfonamido)pentan-2-yl)carbamate (15a) is afforded.

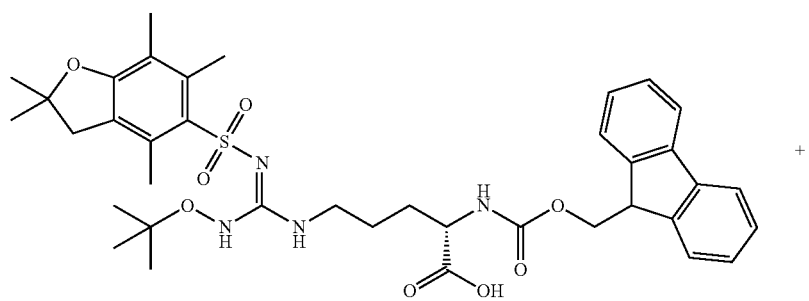

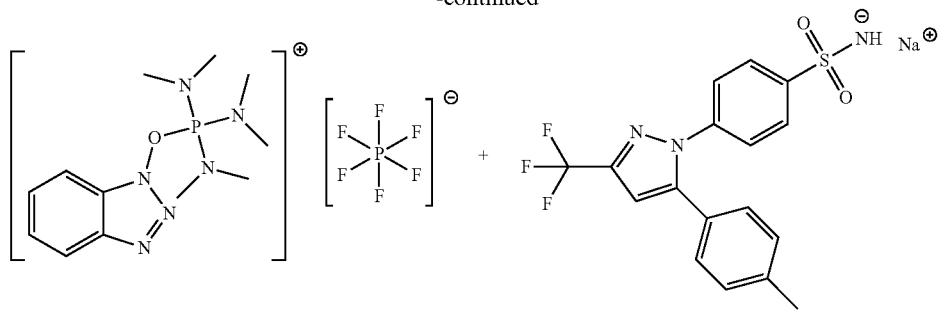

(2a)

1. CH₂Cl₂
2. add triethylamine

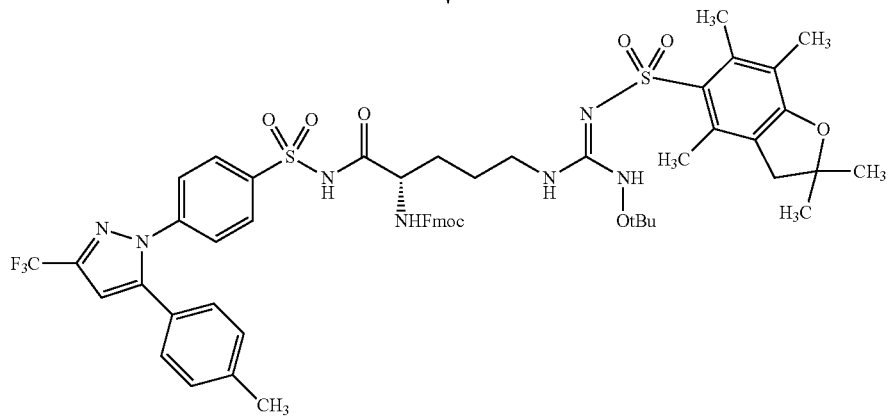

(15a)

Step 2: Compound (15a) is treated with 20-50% piperidine in N,N-dimethylformamide (0.1 M) to remove the Fmoc protecting group. The residue is purified by reverse phase chromatography (acetonitrile/water with 0.05% trifluoroacetic acid) and then dissolved in 95% trifluoroacetic acid-methylene chloride (0.1 M). The mixture is stirred at 25° C. for 6 h and then concentrated under reduced pressure. The residue is purified by reverse phase chromatography (acetonitrile/water with 0.05% trifluoroacetic acid) to provide the title compound.

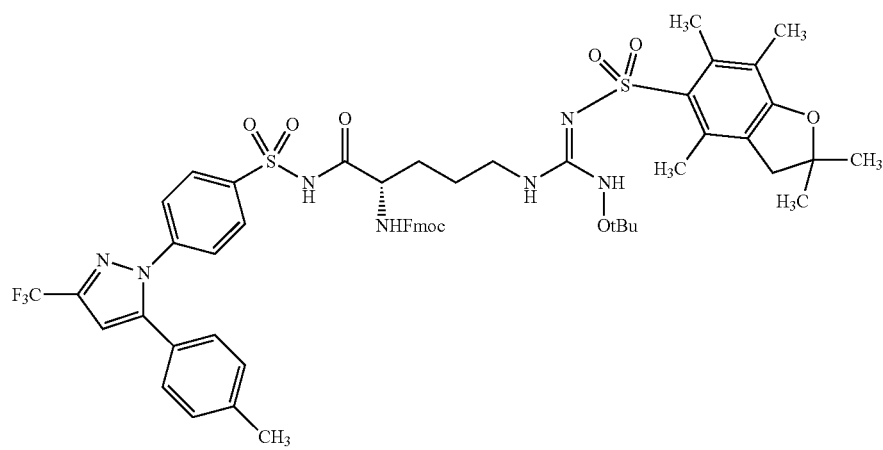

(15a)

1. 20-50% piperidine in DMF
2. 95% trifluoroacetic acid-CH₂Cl₂

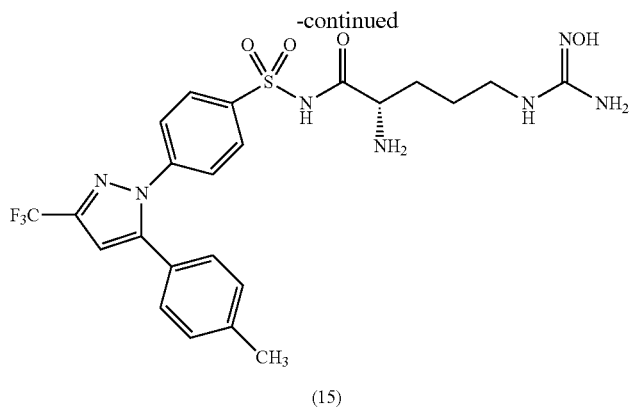

(15)

Example 16

(S)-2-Acetamido-5-(2-hydroxyguanidino)-N-((4-(5-(p-tolyl)-3-(trifluoromethyl)-1H-pyrazol-1-yl)phenyl)sulfonyl)pentanamide

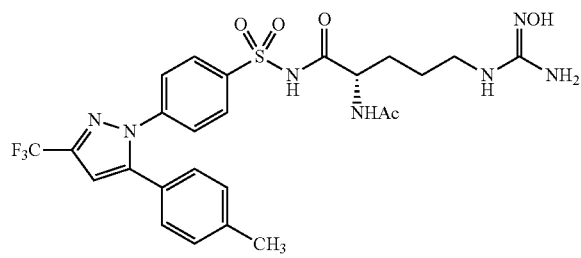

Compound (15a) is treated with 20-50% piperidine in N,N-dimethylformamide (0.1 M). After 10 min the reaction is concentrated and the residue is purified using reverse phase chromatography (acetonitrile/water with 0.05% trifluoroacetic acid) to provide the free primary amine. This amine (1.0 eq.) is dissolved in pyridine (0.25 M) and acetic anhydride (1.2 eq.) is added to acylate the primary amine, after 1 h the reaction is quenched with aqueous acid, extracted with ethyl acetate, and purified by chromatography. The residue is dissolved in 95% trifluoroacetic acid-methylene chloride (0.1 M). The mixture is stirred at 25° C. for 6 h and then concentrated under reduced pressure. The residue is purified by reverse phase chromatography (acetonitrile/water with 0.05% trifluoroacetic acid) to provide the title compound.

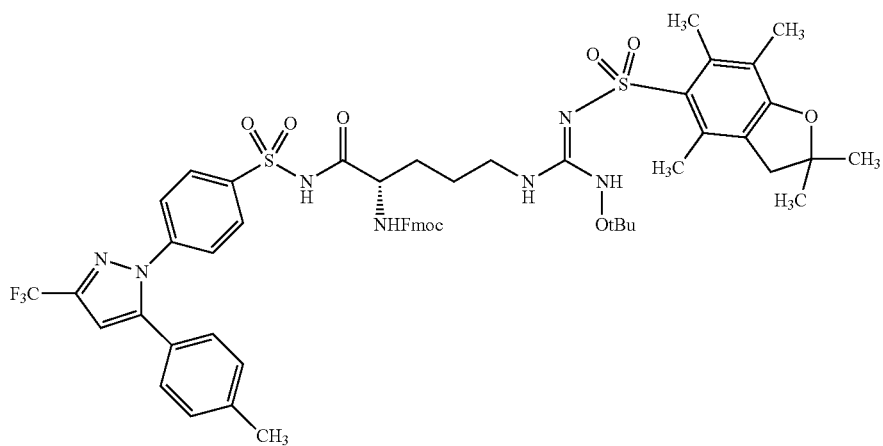

(15a)

1. 20-50% piperidine in DMF (removal of protecting group)
2. pyridine and acetic anhydride (acylate primary amine)

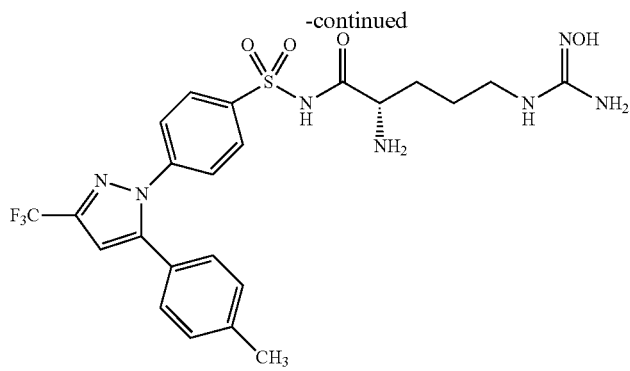

Example 17

(S)-2-formamido-5-(2-hydroxyguanidino)-N-((4-(5-(p-tolyl)-3-(trifluoromethyl)-1H-pyrazol-1-yl)phenyl)sulfonyl)pentanamide

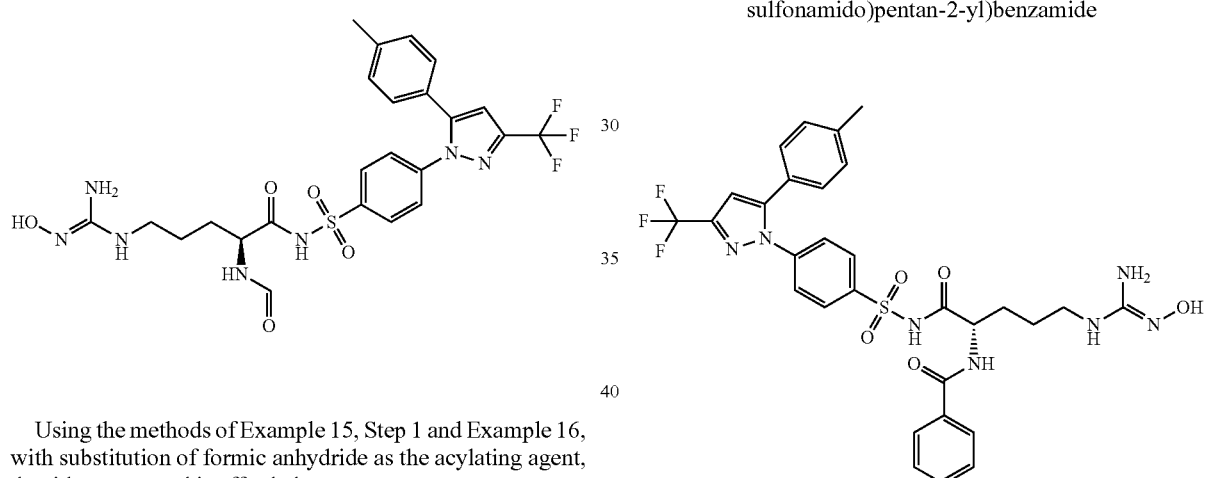

Using the methods of Example 15, Step 1 and Example 16, with substitution of formic anhydride as the acylating agent, the title compound is afforded.

Example 18

(S)-5-(2-hydroxyguanidino)-2-propionamido-N-((4-(5-(p-tolyl)-3-(trifluoromethyl)-1H-pyrazol-1-yl)phenyl)sulfonyl)pentanamide Using the methods of Example 15, Step 1 and Example 16, with substitution of propionic anhydride as the acylating agent, the title compound is afforded.

Example 19

(S)—N-(5-(2-hydroxyguanidino)-1-oxo-1-(4-(5-(p-tolyl)-3-(trifluoromethyl)-1H-pyrazol-1-yl)phenylsulfonamido)pentan-2-yl)benzamide Using the methods of Example 15, Step 1 and Example 16, with substitution of benzoic anhydride as the acylating agent, the title compound is afforded.

Example 20

(S)-2-Amino-6-(2-hydroxyguanidino)-N-((4-(5-(p-tolyl)-3-(trifluoromethyl)-1H-pyrazol-1-yl)phenyl)sulfonyl)hexanamide

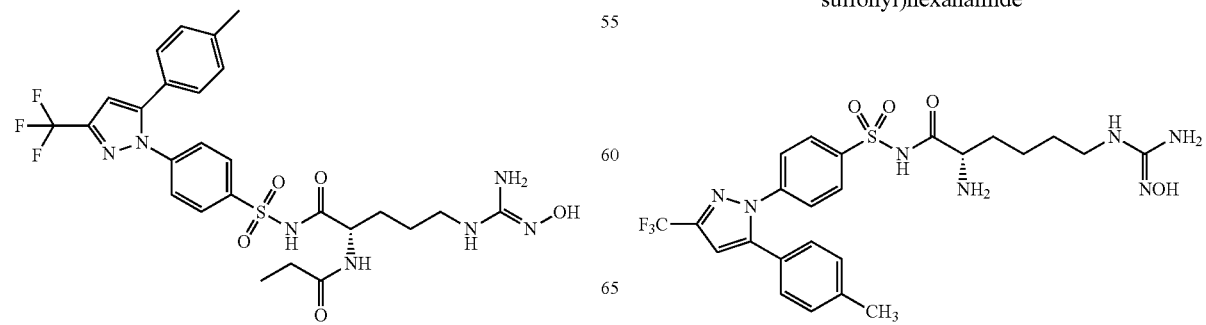

Step 1: (S)-2-((((9H-Fluoren-9-yl)methoxy)carbonyl)amino)-6-(3-(tert-butoxy)-2-((2,2,4,6,7-pentamethyl-2,3-dihydrobenzofuran-5-yl)sulfonyl)guanidino)hexanoic acid (Fmoc-L-HomoArg(tBuO)(Pbf)-OH) can be made by a procedure similar to the synthesis of (Fmoc-L-Arg(tBuO)(Pbf)-OH) as described in "Preparation of NG-Substituted L-Arginine Analogues Suitable for Solid Phase Peptide Synthesis" Martin et. al.; *J. Org. Chem.*, 2008, 73 (19), pp 7849-7851. Using the methods of Example 5, Step 2, with substitution of (Fmoc-L-HomoArg(tBuO)(Pbf)-OH) for Example 5 reagent (S)-2-(tert-Butoxycarbonylamino)-5-(3-(2,2,4,6,7-pentamethyl-2,3-dihydrobenzofuran-5-ylsulfonyl)guanidino)pentanoic acid (Boc-L-Arg(Pbf)-OH) (1.25 eq.) the intermediate compound (S)-(9H-Fluoren-9-yl)methyl (6-(3-(tert-butoxy)-2-((2,2,4,6,7-pentamethyl-2,3-dihydrobenzofuran-5-yl)sulfonyl)guanidino)-1-oxo-1-(4-(5-(p-tolyl)-3-(trifluoromethyl)-1H-pyrazol-1-yl)phenylsulfonamido)hexan-2-yl) carbamate (20a) is afforded.

Step 2: Using the methods of Example 15, Step 2, (20a) is treated to afford the title compound.

Example 21

(S)-2-Acetamido-6-(2-hydroxyguanidino)-N-((4-(5-(p-tolyl)-3-(trifluoromethyl)-1H-pyrazol-1-yl)phenyl)sulfonyl)hexanamide

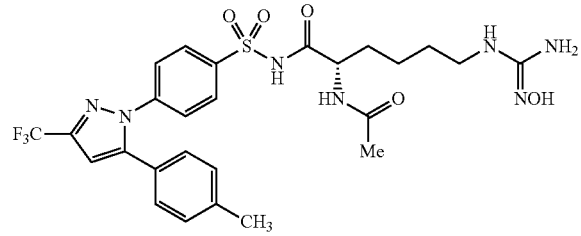

Compound (20a) is treated according to the methods of Example 16 to afford the title compound.

Example 22

(S)-2-Formamido-6-(2-hydroxyguanidino)-N-((4-(5-(p-tolyl)-3-(trifluoromethyl)-1H-pyrazol-1-yl)phenyl)sulfonyl)hexanamide

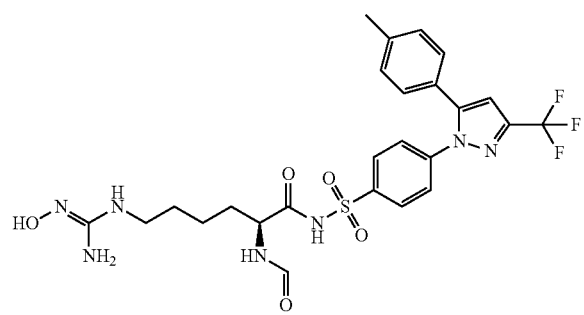 [SMILES: Cc1ccc(-c2cc(C(F)(F)F)nn2-c2ccc(S(=O)(=O)NC(=O)[C@H](CCCCN/C(N)=N/O)NC=O)cc2)cc1]

Compound (20a) is treated according to the methods of Example 16, with substitution of formic anhydride as the acylating agent, to afford the title compound.

Example 23

(S)-6-(2-Hydroxyguanidino)-2-propionamido-N-((4-(5-(p-tolyl)-3-(trifluoromethyl)-1H-pyrazol-1-yl)phenyl)sulfonyl)hexanamide

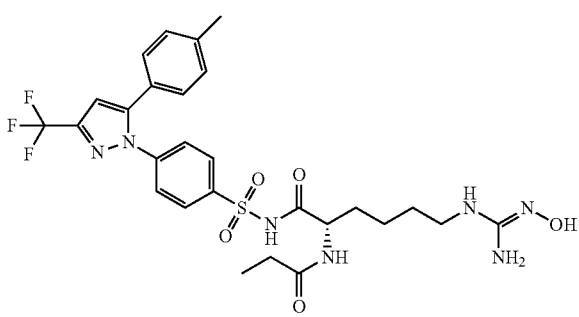 [SMILES: CCC(=O)N[C@@H](CCCCN/C(N)=N/O)C(=O)NS(=O)(=O)c1ccc(-n2nc(C(F)(F)F)cc2-c2ccc(C)cc2)cc1]

Compound (20a) is treated according to the methods of Example 16, with substitution of propionic anhydride as the acylating agent, to afford the title compound.

Example 24

(S)—N-(6-(2-Hydroxyguanidino)-1-oxo-1-(4-(5-(p-tolyl)-3-(trifluoromethyl)-1H-pyrazol-1-yl)phenylsulfonamido)hexan-2-yl)benzamide

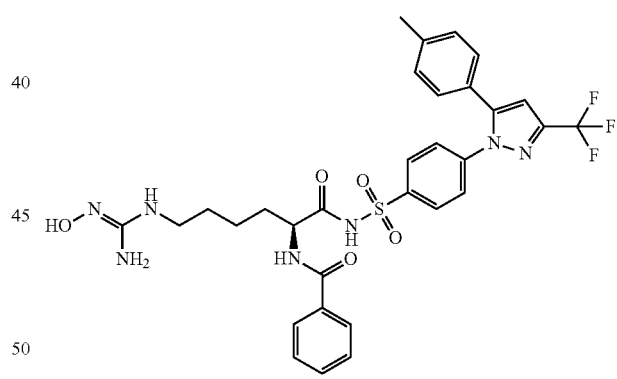

Compound (20a) is treated according to the methods of Example 16, with substitution of benzoic anhydride as the acylating agent, to afford the title compound.

E. Method of Treatment

A compound of Formula (I), as used herein, is meant to include a pharmaceutically acceptable salt, or solvate of a compound or salt, of Formula (I).

The present invention further provides methods for treating a disease condition in a subject having or susceptible to having such a disease condition, by administering to the subject a therapeutically-effective amount of one or more compounds as described in Formula (I). In one embodiment, the treatment is preventative treatment. In another embodiment, the treatment is palliative treatment. In another embodiment, the treatment is restorative treatment. In another embodiment, the subject is a mammal. In yet another embodiment, the subject is a human.

1. Conditions

The conditions that can be treated in accordance with the present invention include, but are not limited to, autoimmune disorders, chronic inflammatory disorders, acute inflammatory disorders, auto-inflammatory disorders, pain, cancer, neoplasia, lung cancer, colorectal cancer and the like. Conditions that can be treated in accordance with the present invention also include arginine deficiency disorders, including conditions, for example, where there is an elevated level of arginase present in patients with chronic hemolytic anemias such as sickle cell disease and paroxysmal nocturnal hemoglobinuria.

In some embodiments, methods described herein are used to treat or prevent a disease condition comprising administering to a subject in need thereof a therapeutically effective amount of a compound of Formula (I), wherein the condition is selected from the group consisting of non-small cell lung cancer, skin cancer, liver cancer, metastatic colorectal cancer (and FAP), renal cell cancer glioblastoma, squamous cell cancer, bladder cancer, breast cancer, biliary tract cancer, cervical cancer, prostate cancer, small cell lung cancer, ovarian cancer, pancreatic cancer, gastrointestinal cancer and CNS cancer.

In some embodiments, methods described herein are used to treat a disease condition comprising administering to a subject in need thereof a therapeutically effective amount of a compound of Formula (I), wherein the condition is selected from the group consisting of actinic keratosis, cystic fibrosis and acne.

In some embodiments, methods described herein are used for healing wounds by administering to a subject in need thereof a therapeutically effective amount of a compound of Formula (I).

In some embodiments, methods described herein are used to treat a disease condition comprising administering to a subject in need thereof a therapeutically effective amount of a compound of Formula (I), wherein the condition is non-small cell lung cancer In some embodiments the methods described herein are used to treat patients with disorders arising from dysregulated enzymes and/or inflammatory mediator production, stability, secretion and posttranslational processing. Examples of inflammatory mediators that may be dysregulated include nitric oxide, prostaglandins and leukotrienes. Examples of enzymes include cyclo-oxygenase and nitric oxide synthase.

In some embodiments, the methods described herein are used to treat a patient in need thereof suffering from an autoimmune disorder, chronic and/or acute inflammatory disorder and/or auto-inflammatory disorder. Examples of disorders include, but are not limited to arthritis, rheumatoid arthritis, osteoarthritis, juvenile arthritis, psoriatic arthritis.

In some embodiments, the methods described herein can be used to treat a patient in need thereof and suffering from neoplasia. Examples of these conditions include but are not limited to the following:

| | | |
|---|---|---|
| acral lentiginous melanoma | fibrolamellar carcinoma | neuroepithelial adenocarcinoma nodular melanoma |
| actinic keratoses | focal nodular hyperplasia | oat cell carcinoma |
| adenocarcinoma | gastrinoma | oligodendroglial |
| adenoid cycstic carcinoma | germ cell tumors | osteosarcoma |
| adenomas | glioblastoma | pancreatic cancer |
| adenosarcoma | glucagonoma | papillary serous adenocarcinoma |
| adenosquamous carcinoma | hemangiblastomas | pineal cell |
| astrocytic tumors | hemangioendothelioma | pituitary tumors |
| bartholin gland carcinoma | hemangiomas | plasmacytoma |
| basal cell carcinoma | hepatic adenoma | pseudosarcoma |
| bronchial gland carcinomas | hepatic adenomatosis | pulmonary blastoma |
| capillary | hepatocellular carcinoma | renal cell carcinoma |
| carcinoids | insulinoma | retinoblastoma |
| carcinoma | intaepithelial neoplasia | rhabdomyosarcoma |
| carcinosarcoma | interepithelial squamous cell neoplasia | sarcoma |
| cavernous | invasive squamous cell carcinoma | serous carcinoma |
| cholangiocarcinoma | large cell carcinoma | small cell carcinoma |
| chondosarcoma | leiomyosarcoma | soft tissue carcinomas |
| Choroid plexus papilloma/carcinoma | lentigo maligna melanomas | somatostatin-secreting tumor |
| clear cell carcinoma | malignant melanoma | squamous carcinoma |
| cystadenoma | malignant mesothelial tumors | squamous cell carcinoma |
| endodermal sinus tumor | medulloblastoma | submesothelial |
| endometrial hyperplasia | medulloepithelioma | superficial spreading melanoma |
| endometrial stromal sarcoma | melanoma | undifferentiatied carcinoma |
| endometrioid adenocarcinoma | meningeal | uveal melanoma |
| ependymal | mesothelial | verrucous carcinoma |
| epitheloid | metastatic carcinoma | vipoma |
| Ewing's sarcoma | mucoepidermoid carcinoma | well differentiated carcinoma |
| familial adenomatous polyposis (FAP) | neuroblastoma | Wilm's tumor |

The term patient refers to both humans and non-human animals with the above-mentioned conditions. Non-human animals could be companion animals such as, but not limited to, canine and feline species.

2. Subjects

Suitable subjects to be treated according to the present invention include mammalian subjects. Mammals according to the present invention include, but are not limited to, human, canine, feline, bovine, caprine, equine, ovine, porcine, rodents, lagomorphs, primates, and the like, and encompass mammals in utero. Subjects may be of either gender and at any stage of development.

3. Administration and Dosing

A compound of the present invention may be administered in the form of a prodrug in a therapeutically effective amount.

The compounds of the present invention can be administered by any suitable route in the form of a pharmaceutical composition adapted to such a route, and in a dose effective for the treatment intended. Therapeutically effective doses of the compounds of the present invention required to prevent or arrest the progress of, or to treat the medical condition, are readily ascertained by one of ordinary skill in the art using preclinical and clinical approaches familiar to the medicinal arts.

For convenience the compounds of the present invention can be administered in a unit dosage form. If desired, multiple doses per day of the unit dosage form can be used to increase the total daily dose. The unit dosage form, for example, may be a tablet or capsule containing about 0.01, 0.05, 0.1, 0.5, 1, 5, 10, 15, 20, 25, 30, 35, 40, 45, 50, 55, 60, 65, 70, 75, 80, 85, 90, 95, 100, 125, 150, 175, 200, 250 or 500 mg of the compound of the present invention. In one embodiment, the unit dosage form contains from about 0.01 mg to about 500 mg of the compound of the present invention. In another embodiment, the unit dosage form contains from about 0.02 to about 400 mg of the compound of the present invention. In another embodiment, the unit dosage form contains from about 0.05 mg to about 250 mg of the compound of the present invention. In another embodiment, the unit dosage form contains from about 0.1 mg to about 200 mg of the compound of the present invention. In another embodiment, the unit dosage form contains from about 0.5 mg to about 150 mg of the compound of the present invention. In another embodiment, the unit dosage form contains from about 1.0 mg to about 100 mg of the compound of the present invention.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary based on the specific situation. Dosage levels from about 0.001 mg to about 100 mg of the compound of the present invention per kilogram of body weight per day are useful in the treatment of the above-indicated conditions. In one embodiment, the total daily dose of the compound of the present invention (administered in single or divided doses) is typically from about 0.001 mg/kg to about 20 mg/kg (i.e., mg compound/kg body weight). In another embodiment, the total daily dose of the compound of the present invention is from about 0.005 mg/kg to about 10 mg/kg. In another embodiment, the total daily dose is from about 0.005 mg/kg to about 5 mg/kg. In another embodiment, the total daily dose is from about 0.01 mg/kg to about 1 mg/kg. In another embodiment, the total daily dose is from about 0.8 mg/kg to about 15 mg/kg. In another embodiment, the total daily dose is from about 0.2 mg/kg to about 4 mg/kg. These dosages are based on an average human subject having a weight of about 65 kg to about 75 kg. A physician will readily be able to determine doses for subjects whose weight falls outside of this range, such as infants. The administration of the compound of the present invention can be repeated a plurality of times in a day (typically no greater than 4 times) to achieve the desired daily dose.

The present invention further comprises use of a compound of the present invention as a medicament (such as a unit dosage tablet or unit dosage capsule).

In another embodiment, the present invention comprises the use of a compound of the present invention for the manufacture of a medicament (such as a unit dosage tablet or unit dosage capsule) to treat one or more of the conditions previously identified in the above sections discussing methods of treatment. In one embodiment, the condition is cancer. In another embodiment the condition is an inflammatory condition.

F. Pharmaceutical Compositions

For treatment of the conditions referred to above, the compounds described herein can be administered as follows:

1. Oral Administration

The compounds of the present invention may be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges, pills, cachets, and hard and soft capsules, which can contain liquids, gels, or powders.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable lubricants, for use in a tablet, may be present in amounts from about 0.1% to about 5% by weight, and include calcium, zinc or magnesium stearate, sodium stearyl fumarate and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

In another embodiment, a pharmaceutical composition comprises a therapeutically effective amount of a compound of Formula (I) or a pharmaceutically acceptable salt thereof, and a pharmaceutically acceptable carrier.

2. Parenteral Administration

Compounds of the present invention may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Prodrug compounds of the invention exhibit high water-solubility and thus are particularly suitable for use as injectable formulations and intravenous (IV) therapy. When a prodrug of the invention is administered parenterally (e.g., intravenously or intramuscularly), a preparation of a sterile injectable aqueous solution may be formulated using suitable dispersing, wetting and suspension agents. The sterile injectable preparation may also include non-toxic parenterally-acceptable diluents or solvents, such as a solution in propylene glycol. The sterile injectable preparation may also be a re-constitutable sterile powder for dissolution in pharmaceutically-acceptable vehicles, such as distilled water, Ringer's solution and isotonic sodium chloride solution. Also useful as solvent or suspension agents are mono- or diglycerides and fatty acids, such as oleic acid. These injectable formulations would be especially useful in treatment or management of post-operative pain. In another embodiment, a pharmaceutical composition of the present invention comprises a therapeutically-effective amount of a compound of Formula (I) in a formulation suitable for parenteral administration as intravenous therapy or as an injectable to treat post-operative pain. In another embodiment, suitable compounds for parenteral formulation are compounds of Formula (I) wherein n is 1, 2, 3, or 4; $R^{11}$ is H or hydroxyl; and $R^{12}$ is H or acyl. In another embodiment, such suitable compounds for parenteral formulation are compounds of Formula (I) wherein $R^{12}$ is H.

Compositions for parenteral administration may be formulated as immediate or modified release, including delayed or sustained release.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

3. Topical Administration

Compounds of the present invention may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

4. Rectal Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

G. Combinations and Combination Therapy

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, cytostatic drugs, anti-proliferative agents and angiogenesis inhibitors.

In another embodiment, the one or more additional pharmaceutically active compounds is selected from the group consisting of anti-cancer drugs and anti-inflammatory drugs.

NO-releasing coxib conjugate described herein are also optionally used in combination with other therapeutic reagents that are selected for their therapeutic value for the condition to be treated. In general, the compounds described herein and, in embodiments where combinational therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer an NO-releasing coxib conjugate, as described herein, in combination with another therapeutic agent or NO-releasing coxib conjugate. By way of example only, the therapeutic effectiveness of an NO-releasing coxib conjugate is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an NO-releasing coxib conjugate as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, an NO-releasing coxib conjugate is optionally used in combination with procedures that provide additional benefit to the patient. An NO-releasing coxib conjugate and any additional therapies are optionally administered before, during or after the occurrence of a disease or condition, and the timing of administering the composition containing an NO-releasing coxib varies in some embodiments. Thus, for example, an NO-releasing coxib conjugate is used as a prophylactic and is administered continuously to subjects with a propensity to develop conditions or diseases in order to prevent the occurrence of the disease or condition. An NO-releasing coxib conjugate is optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A NO-releasing coxib conjugate can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases an NO-releasing coxib conjugate may be optimally used together with one or more of the following non-limiting examples of anti-cancer agents. A first example, alkylating agents, includes but is not limited to cisplatin (PLATIN), carboplatin (PARAPLATIN), streptozocin (ZANOSAR), busulfan (MYLERAN) and cyclophosphamide (ENDOXAN). A second example, anti-metabolites, includes but is not limited to mercaptopurine (PURINETHOL), thioguanine, pentostatin (NIPENT), cytosine arabinoside (ARA-C) and methotrexate (RHEUMATREX). A third example, plant alkaloids and terpenoids, includes but is not limited to vincristine (ONCOVIN), vinblastine and paclitaxel (TAXOL). A fourth example, topoisomerase inhibitors, includes but is not limited to irinotecan (CAMPTOSAR), topotecan (HYCAMTIN) and etoposide (EPOSIN). A fifth example, cytotoxic antibiotics, includes but is not limited to actinomycin D (COSMEGEN), doxorubicin (ADRIAMYCIN), bleomycin (BLENOXANE) and mitomycin (MITOSOL). A sixth example, angiogenesis inhibitors, includes but is not limited to sunitinib (SUTENT) and bevacizumab (AVASTIN). A seventh example, tyrosine kinase inhibitors, includes but is not limited to imatinib (GLEEVEC), erlotinib (TARCEVA), lapatininb (TYKERB) and axitinib (INLYTA).

Where a subject is suffering from or at risk of suffering from an inflammatory condition, an NO-releasing coxib conjugate described herein is optionally used together with one or more agents or methods for treating an inflammatory condition in any combination. Therapeutic agents/treatments for treating an autoimmune and/or inflammatory condition include, but are not limited to any of the following examples. A first example, corticosteroids, includes but is not limited to cortisone, dexamethasone, and methylprednisolone. A second example, nonsteroidal anti-inflammatory drugs (NSAID's), includes but is not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONS TEL), nabumetone (RELAFEN) and piroxicam (FELDENE). A third example, immunosuppressants, includes but is not limited to methotrexate (RHEUMATREX), leflunomide (ARAVA), azathioprine (IMURAN), cyclosporine (NEORAL, SANDIMMUNE), tacrolimus and cyclophosphamide (CYTOXAN). A fourth example, CD20 blockers, includes but is not limited to rituximab (RITUXAN). A fifth example, Tumor Necrosis Factor (TNF) blockers, includes but is not limited to etanercept (ENBREL), infliximab (REMICADE) and adalimumab (HUMIRA). A sixth example, interleukin-1 receptor antagonists, includes but is not limited to anakinra (KINERET). A seventh example, interleukin-6 inhibitors, includes but is not limited to tocilizumab (ACTEMRA). An eighth example, interleukin-17 inhibitors, includes but is not limited to AIN457. A ninth example, Janus kinase inhibitors, includes but is not limited to tasocitinib. A tenth example, syk inhibitors, includes but is not limited to fostamatinib.

H. Kits

The present invention further comprises kits that are suitable for use in performing the methods of treatment or prevention described above. In one embodiment, the kit contains a first dosage form comprising one or more of the compounds of the present invention and a container for the dosage, in quantities sufficient to carry out the methods of the present invention.

I. Biological Assays

Compound Metabolism in Plasma: The present invention includes compounds that are enzymatically activated in vivo to produce coxibs. Compounds are analyzed, after incubation in plasma, for the rate of disappearance of the compound species and appearance of coxib and/or intermediate compounds.

Rat Air-Pouch Model for Acute Inflammation

A study of celecoxib release from Example Compound 5 is assessed by measurement of PGE2 levels, which are indicative of inflammatory response.

Animals: Sprague-Dawley rats (Charles River Laboratories, R #3234, PO #738990, male, 160-180 g) were received, individually examined, and housed in cages of five rats each. The rats were ear notched for identification purposes.

Compounds and dosing solutions: The vehicle was prepared by dissolving 40 g (2-hydroxypropyl)-β-cyclodextrin (HP-β-CD, Sigma, Cat. 332593, lot MKBJ5858V) in 160 mL sterile saline for injection, USP (Hospira, lot 26-801-FW) making a 25% solution which was filter sterilized (0.2 μm, Nalgene, Cat. 151-4020, lot 1095610). A 1% carrageenan solution was prepared by dissolving g λ-carrageenan (Fluka, Cat. 22049, lot 1318338) in hot 60 mL sterile saline for injection, USP. This solution was stored at 4-8° C. Test compounds were dissolved in DMSO (Fisher Scientific, Cat. D128-500, lot 874999) to make 75 mM stocks. 0.25 mL of compound DMSO stocks were mixed with 12.5 mL of HP-β-CD solution at 50° C. (maximum DMSO concentration was 2% of the final volume of vehicle). Final concentration of all test compounds was 1.5 mM and compounds were dosed within 2 hours of preparation at 0.01 mmol/kg (12 nmol of test compound per rat).

Day 0—Air pouch initiation: The rats were anesthetized in a biological cabinet, the nape of the neck was cleansed with 70% isopropanol (Butler Schein Animal Health, Cat. 002498, lot 29EMS07104547) followed by 1% povidone-iodine solution (Ricca Chemical Co., Cat. 3955-16, lot 2205469). Twenty mL of sterile (0.22 μm, Millipore, Cat. SLGP033RS, lot R2KA55925, exp 08/2015) air was injected subcutaneously (SC) using a 23G×1½ inch needle fixed to a 20 mL syringe. The rats were returned to routine housing. No adverse reactions were observed.

Day 3—Air pouch maintenance: The rats were anesthetized in a biological cabinet, the nape of the neck was cleansed with 70% isopropanol followed by 1% povidone-iodine solution. Ten mL of sterile air was injected SC using a 23G×1½ inch needle fixed to a 20 mL syringe. The rats were returned to routine housing in clean cages. No adverse reactions were observed.

Day 6—Compound administration and carrageenan insult: At commencement of the study, each rat was weighed and sorted into treatment groups of 5 rats/group based upon average weight. Each rat was dosed orally via gavage at 6.809 mL/kg (1.6 mL/235 g) with their respective test material/vehicle. Two hours after test material/vehicle administration, the rats were injected with 1.0 mL of the room temperature 1% carrageenan saline solution into the air pouch. Four hours after carrageenan injection, the rats were anesthetized and 5 mL of the exudate buffer was injected into the air pouch. The pouch was gently massaged, the exudate immediately removed, and exudate volume recorded. The exudate was collected in a serum separator tube on an ice bath. The exudates were centrifuged (refrigerated) and an aliquot of the supernatant was stored in a labeled Eppendorf tube at −80° C.

Termination of Study: Animals were euthanized via $CO_2$ asphyxiation at the completion of the in-life portion of this study and carcasses were disposed of according to standard protocols.

Data analysis: The exudate samples were thawed to room temperature and assayed by ELISA for $PGE_2$ (R&D Systems, Cat. KGE004B, lot 307711). Statistical significance of treatments on mean exudate volumes are determined by comparison of means for treatment groups with vehicle group. Mean cytokine concentrations and standard deviations are determined for each group. Statistical significance of treatments on cytokine concentrations are determined for each compound group compared to vehicle group. Statistical significance (p-value) was calculated vs control groups by Student's t-Test.

$PGE_2$ Measurements: Oral administration of 6.809 ml/kg of vehicle (negative control) two hours prior to intra-pouch challenge with 1% carrageenan resulted in a collected exudate volume of 5.7 ml and 4358 pg/ml $PGE_2$ in the exudate. Pretreatment with orally administered 0.01 mmol/kg celecoxib (positive control) resulted in a significant 19% reduction in collected exudate volume and an 80% reduction in exudate $PGE_2$ release. Oral pretreatment with 0.01 mmol/kg of test compound (5) resulted in a significant 24% reduction in collected exudate volume and an 80% reduction in exudate $PGE_2$ release, similar to that observed with celecoxib.

TABLE 6

| Results | Group | Volume (mL) | $PGE_2$ (pg/mL) |
| --- | --- | --- | --- |
| Mean | Vehicle | 5.7 | 4357.7 |
| SD | | 0.2 | 1122.0 |
| Mean | celecoxib | 4.6 | 907.1 |
| SD | | 0.3 | 258.4 |
| p-value | | 0.0002 | 0.0002 |
| Mean | Example 5 | 4.3 | 896.0 |
| SD | | 0.5 | 104.1 |
| p-value | | 0.001 | 0.0001 |

Plasma & Microsomal Stability: The present invention includes compounds that are enzymatically activated in vivo to produce coxibs. Compounds are analyzed, after incubation in plasma or liver microsomes, for the rate of disappearance of the compound species.

Compounds (1 μM) will be incubated, in triplicate, in rat plasma or liver microsomes at 37° C. and analyzed by LC/MS/MS (T=0, 10, 20, 30, 45 and 60 min). Reaction is quenched by acetonitrile. Analysis used will be standard reverse phase HPLC and API 4000 triple quadrupole mass spectrometry. Elimination rate constant, in vitro half-life and intrinsic clearance are calculated from results. Plasma results using LC/MS/MS will also verify results using HPLC-UV/ELSD.

Selectivity: Evaluation of COX-1 & COX-2 Activity In Vitro: The present invention includes compounds that are coxib conjugates, therefore they will be evaluated for selective COX-1 or COX-2 inhibition. Assays for COX-1 and COX-2 activity in vitro are described in U.S. Pat. No. 5,760,068.

Preparation of Recombinant COX-1 and COX-2:
(1) A fragment containing the coding region of either human or murine COX-1 or COX-2 is cloned into a BamH1 site of a baculovirus transfer vector to generate transfer vectors for COX-I and COX-II.
(2) Recombinant baculoviruses are isolated by transfecting baculovirus transfer vector DNA into SF9 insect cells.
(3) Recombinant viruses are purified and high titer stocks of virus are prepared.
(4) SF9 insect cells are infected with the recombinant baculovirus stock. After 72 hours the cells are centrifuged and the cell pellet homogenized. The homogenate is centrifuged and the supernatant is assayed for COX activity.

Assay for COX-1 and COX-2 activity:
(1) COX activity is assayed as $PGE_2$ formed/μg protein/time using an ELISA to detect the prostaglandin formed.
(2) Insect cell membranes containing the appropriate COX enzyme are incubated in buffer containing arachidonic acid.
(3) Compounds are pre-incubated with the enzyme for 10-20 minutes prior to the addition of arachidonic acid.
(4) Reaction between the arachidonic acid and the enzyme is stopped after ten minutes, and the $PGE_2$ formed is measured by standard ELISA technology.

Assessment of Anti-Cancer Activity of Test Compounds by MTT Based Cell Proliferation Assay Anti-tumor growth potential of test compounds are evaluated in vitro using various human tumor cells, available from the American Type Culture Collection (ATCC), such as A549 lung tumor cells, DU145 prostate tumor cells, HT29 colon cancer cells, MIA PaCa-2 pancreatic cancer cells, MCF-7 ($ER^+$) breast tumor cells and BEAS-2B cells (immortalized normal lung epithelial cells) as control [Hida, et al., Clin. Cancer Res. 6, 2006-2011 (2000)]. Test compound effect on cell proliferation will be determined using the MTT based cell proliferation assay. MTT based cell proliferation assays are described in U.S. Pat. No. 8,143,237.

MTT [3-(4,5-dimethylthiazol-2-yl)-2,5-diphenyltetrazolium bromide] incorporation based cell proliferation assay is performed using the MTT cell proliferation assay kit (Roche Applied Sciences, Germany). The assay is carried out according to the instruction provided by the vendor. Briefly, equal numbers of cells are plated in 96-well flat-bottomed plates and are incubated with test compounds at various concentrations for a period of three days. Vehicle control culture wells receive an equal volume of vehicle solution. Thereafter, 0.5 mg/ml of MTT reagent is added to each well and the microplate is incubated further for 4 hours at 37° C. in presence of 5% $CO_2$. Cells are then solubilized by adding solubilizing solution and allowed to incubate at 37° C. overnight. After complete solubilization of the formazan crystals, the absorbance is read at 540 nm in a microplate reader (BioRad, USA). The results (mean optical density (OD)±standard dethroughtion (SD)) obtained from quadruplicate wells are used to calculate the inhibition of cell proliferation (50% of inhibitory concentration, $IC_{50}$) of the test compounds.

Suppression of Lung Cancer Cell Migration: Efficacy testing will be done to evaluate test compound suppression of lung cancer cell migration, a model of metastasis. Methods to evaluate lung cancer cell migration are described in Park, et al. Mol. Med. Reports 3, 1007-1013 (2010).

Cell Culture: Human lung cancer cells A549 are obtained from American Type Culture Collection (ATCC, Manassas, Va.). Cells are incubated in RPMI-1640 medium supplemented with 10% fetal bovine serum (FBS) and penicillin/streptomycin (GibcoBRL, Grand Island, N.Y., USA).

Monolayer Wound Healing Assay: Cell proliferation in confluent A549 monolayers is blocked by a 30 minute pre-incubation in the presence of mitomycin C (3 μg/ml). Test compounds, in cell culture buffer, are added to confluent monolayers 30 minutes before wound induction. A549 monolayers are subsequently scratched with a pipette tip. Wound areas are evaluated with phase contrast microscopy on an inverted microscope. Images of the same areas are obtained at intervals from zero to 96 hours. Cell migration rate through wound healing is evaluated from the images using Paint.Net v.3.10 software. Cell migration is expressed as the fold change in the migration area, relative to untreated control cells at the same time period.

Compound Formulations for Intravenous (IV), Oral Gavage (PO) or Intraperitoneal (IP) Administration: Compounds will be formulated for administration using 25% hydroxypropyl-beta-cyclodextrin-PBS buffer (HBCD-PBS) at 1 mg/ml. HBCD-PBS is the preferred formulation media for compound administration. Additional formulation vehicles may also be used, including 2% Tween 80 in saline, and 20% polyethylene glycol (PEG-300) in 0.9% sodium chloride in water.

Determination of Maximum Tolerated Dose (MTD) of Test Compounds in Rats: In order to estimate the doses of test compounds for use in efficacy testing in animal models of cancer, it will be determined at what doses adverse events occur. Methods to determine MTD in rats are described in Rao, et al., Mol. Cancer. Ther. 5, 1530-1538 (2006).

In order to determine doses for efficacy studies, the maximum tolerated dose (MTD) is determined. Male F344 rats are fed various concentrations of test compounds for six weeks. MTD is determined based on the highest dose that causes a 10% loss in body weight without mortality or signs of toxicity. Body weights are recorded twice weekly. Animals are examined daily for signs of toxicity. At termination, animals are euthanized and organs dissected and examined.

Compound Metabolism (PK) in Rats: The pharmacokinetics (PK) of compounds will be tested by single dose IV administration to Sprague Dawley rats.

For each test compound, three (3) Sprague Dawley (CD® IGS) male rats are used. Animals are weighed and dosed individually by body weight on the day of treatment. Compounds are administered intravenously (IV), through surgically placed jugular catheters, at 10 mg/kg using 10 ml/kg volume per animal. Animals found in severe distress or a moribund condition are euthanized. Peripheral blood collections are done primarily through venipuncture of the tail or saphenous veins at various times (T=15 min, 30 min, 1 h, 2 h, 4 h, 8 h, and 24 h). Whole blood samples are collected in an EDTA microtainer, processed to plasma by centrifugation, and the plasma frozen at −80° C. Bioanalysis is done using LC/MS/MS methods using standard reverse phase HPLC and API 4000 triple quadrupole mass spectrometry. The amount of compound present will be used to calculate PK parameters $C_{max}$, $T_{max}$ and AUC.

Compound Effects on Blood Pressure: Since COX-2 inhibitors have been shown to have adverse effects on blood pressure in vivo, the effect of the present compounds will be evaluated for blood pressure effects in spontaneously hypertensive rats (SHR).

Thirty-two male, spontaneously hypertensive rats (SHR), 12-weeks old (four groups of eight) will be used in this study. Initially, mean arterial blood pressure (MAP) is measured through tail-cuff daily, throughout the study. Animals undergo 2 days of blood pressure training and 1 day of baseline blood pressure measurements. Animals are weighed and dosed individually by body weight on the day of treatment. Compounds are administered orally (PO) or by intraperitoneal (IP) injection once on Day 1 at 10 mg/kg using 10 ml/kg volume per animal. Blood pressures are monitored for 6 days post-dose. A total of 7 time points are measured: Day 0 for baseline and Days 1, 2, 3, 4, 5, and 6 of the study. Animals found in severe distress or in a moribund condition will be euthanized. Celecoxib is the positive control tested in these studies.

Anti-inflammatory Efficacy: Rat Carrageenan Foot Pad Edema: The compounds of the present invention are conjugates of coxibs, therefore they will be evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-inflammatory Efficacy: Rat Carrageenan-Induced Analgesia Test: The compounds of the present invention are conjugates of coxibs, therefore they will be evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Tumor Growth Inhibition in Xenograft Mouse Model of NSCLC: Efficacy testing will be done in animal models of cancer tumors. Methods to determine tumor growth inhibition in xenograft mouse models of NSCLC are described in Williams, et al., *Clin. Cancer Res.* 7, 724-733 (2001)

Female HRLN nu/nu mice are injected subcutaneously with $1 \times 10^7$ MV-522 cells in 0.1 ml of phosphate-buffered saline. Treatment is initiated when tumors measure 5×5 mm. Mice are weighed and tumors measured by calipers twice weekly. Animals are euthanized and tumors harvested and measured after 67 days or when animal dies. Drug efficacy is measured based on animal survival and tumor growth.

Tumor Growth Inhibition in Xenograft Mouse Model of Colon Cancer: Efficacy testing will be done in animal models of cancer tumors. Methods to determine tumor growth inhibition in xenograft mouse models of colon cancer are described in Carle, et al., *J. Drug Delivery* 2011, 1-9 (Article ID 869027).

Female HRLN nu/nu mice are injected subcutaneously with $5 \times 10^7$ HT-29 cells in 0.1 ml of phosphate-buffered saline. Treatment is initiated when tumors measure 5×5 mm. Mice are weighed and tumors measured by calipers twice weekly. Animals are euthanized and tumors harvested and measured after 67 days or when animal dies. Drug efficacy is measured based on animal survival and tumor growth.

Growth Inhibition of Gallbladder Adenocarcinoma in Transgenic Mice: Efficacy testing will be done in animal models of cancer tumors. Gallbladder adenocarcinoma in transgenic mice is described in Kiguchi, et al., *Mol. Cancer. Ther.* 6, 1709-1717 (2007).

Homozygous BK5.ErbB-2 transgenic mice, that overexpress rat ErbB-2, and nontransgenic littermates receive a control AIN76A diet or an experimental diet containing the test compound for one month. The transgenic mice develop adenocarcinoma of the gallbladder with a 90% incidence. Ultrasound image analysis and histologic evaluation are used to determine compound effects on gall bladder tumor reversion to a milder phenotype and inhibition of tumor progression.

Inhibition of Colon Cancer in Azomethane-Treated Rats: Efficacy testing will be done in animal models of cancer tumors. Colon cancer in azomethane-treated rats is described in Rao, et al., *Mol. Cancer. Ther.* 5, 1530-1538 (2006).

Male F344 rats (Charles River Breeding Laboratories) are given test compounds blended into the diet. Efficacy of test compounds are determined following initiation of azoxymethane-induced colon cancer. Rats are randomly distributed by weight into various groups and housed in cages. Azomethane treated animals are injected subcutaneous (s.c.), twice weekly, at 15 mg/kg body weight. Vehicle-treated groups are injected with normal saline. Rats are placed on control diet or diets containing test compounds, two weeks after the second injection of azomethane or saline. Body weights are measured every two weeks until termination, 52 weeks after the last azoxymethane treatment. Organs are dissected and examined using a dissecting microscope.

Colon tumors with a diameter of >0.4 cm are fixed in 10% neutral buffered formalin for histopathologic evaluation. Test compounds are evaluated for effect on colonocyte proliferation. Proliferating cell nuclear antigen (PCNA) expression is determined by immunohistochemistry. Paraffin-embedded colons are sectioned and mounted on slides. PCNA antibody (PharMingen, San Diego, Calif.), at a 1:200 dilution, is added for 1 hour. Sections are washed, then incubated with secondary anti-rabbit IgG (30 minutes). Following washing, avidin biotin-complex reagent (Vector Laboratories, Burlingame, Calif.) is added. Sections are washed and 3,3"-diaminobenzidine is added and sections are counterstained with hematoxylin. Proliferation index is calculated based on the number of positive cells (brown nucleus) per crypt.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A compound, or pharmaceutically acceptable salt, or solvate of a compound or salt, of Formula (II):

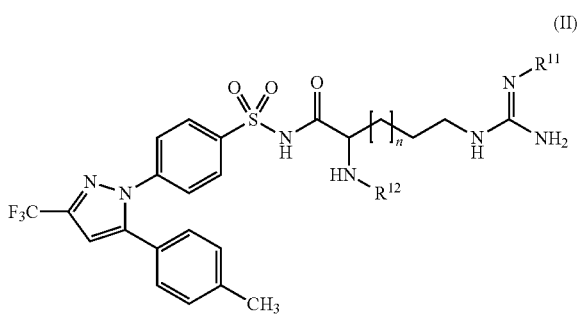

wherein:
n is 1, 2, 3 or 4;
$R^{11}$ is H or hydroxyl; and
$R^{12}$ is selected from the group consisting of H, alkyl, aryl, heteroaryl, arylalkyl, alkoxy, aryloxy, heteroaryloxy, cycloalkyl, heterocycloalkyl, acyl and aroyl.

2. Compound of claim 1, wherein n is 1 or 2; and $R^{11}$ is H.

3. Compound of claim 2, wherein $R^{12}$ is selected from the group consisting of H, acyl, and aroyl.

4. Compound of claim 3, which is selected from the group consisting of:
- (S)-2-Amino-5-guanidino-N-((4-(5-(p-tolyl)-3-(trifluoromethyl)-1H-pyrazol-1-yl)phenyl)sulfonyl)pentanamide;
- (S)-2-Acetamido-5-guanidino-N-((4-(5-(p-tolyl)-3-(trifluoromethyl)-1H-pyrazol-1-yl)phenyl)sulfonyl)pentanamide;
- (S)-2-Formamido-5-guanidino-N-((4-(5-(p-tolyl)-3-(trifluoromethyl)-1H-pyrazol-1-yl)phenyl)sulfonyl)pentanamide;
- (S)-5-Guanidino-2-propionamido-N-((4-(5-(p-tolyl)-3-(trifluoromethyl)-1H-pyrazol-1-yl)phenyl)sulfonyl)pentanamide;
- (S)—N-(5-Guanidino-1-oxo-1-(4-(5-(p-tolyl)-3-(trifluoromethyl)-1H-pyrazol-1-yl)phenylsulfonamido)pentan-2-yl)benzamide;
- (S)-2-Amino-6-guanidino-N-((4-(5-(p-tolyl)-3-(trifluoromethyl)-1H-pyrazol-1-yl)phenyl)sulfonyl)hexanamide;
- (S)-2-Acetamido-6-guanidino-N-((4-(5-(p-tolyl)-3-(trifluoromethyl)-1H-pyrazol-1-yl)phenyl)sulfonyl)hexanamide;
- (S)-2-Formamido-6-guanidino-N-((4-(5-(p-tolyl)-3-(trifluoromethyl)-1H-pyrazol-1-yl)phenyl)sulfonyl)hexanamide;
- (S)-6-Guanidino-2-propionamido-N-((4-(5-(p-tolyl)-3-(trifluoromethyl)-1H-pyrazol-1-yl)phenyl)sulfonyl)hexanamide; and
- (S)—N-(6-Guanidino-1-oxo-1-(4-(5-(p-tolyl)-3-(trifluoromethyl)-1H-pyrazol-1-yl)phenylsulfonamido)hexan-2-yl)benzamide.

5. Compound of claim 1, wherein n is 1 or 2; and $R^{11}$ is hydroxy.

6. Compound of claim 5, wherein $R^{12}$ is selected from the group consisting of H, acyl and aroyl.

7. Compound of claim 6, which is selected from the group consisting of:
- (S)-2-Amino-5-(2-hydroxyguanidino)-N-((4-(5-(p-tolyl)-3-(trifluoromethyl)-1H-pyrazol-1-yl)phenyl)sulfonyl)pentanamide;
- (S)-2-Acetamido-5-(2-hydroxyguanidino)-N-((4-(5-(p-tolyl)-3-(trifluoromethyl)-1H-pyrazol-1-yl)phenyl)sulfonyl)pentanamide;
- (S)-2-formamido-5-(2-hydroxyguanidino)-N-((4-(5-(p-tolyl)-3-(trifluoromethyl)-1H-pyrazol-1-yl)phenyl)sulfonyl)pentanamide;
- (S)-5-(2-hydroxyguanidino)-2-propionamido-N-((4-(5-(p-tolyl)-3-(trifluoromethyl)-1H-pyrazol-1-yl)phenyl)sulfonyl)pentanamide;
- (S)—N-(5-(2-hydroxyguanidino)-1-oxo-1-(4-(5-(p-tolyl)-3-(trifluoromethyl)-1H-pyrazol-1-yl)phenylsulfonamido)pentan-2-yl)benzamide;
- (S)-2-Amino-6-(2-hydroxyguanidino)-N-((4-(5-(p-tolyl)-3-(trifluoromethyl)-1H-pyrazol-1-yl)phenyl)sulfonyl)hexanamide;
- (S)-2-Acetamido-6-(2-hydroxyguanidino)-N-((4-(5-(p-tolyl)-3-(trifluoromethyl)-1H-pyrazol-1-yl)phenyl)sulfonyl)hexanamide;
- (S)-2-Formamido-6-(2-hydroxyguanidino)-N-((4-(5-(p-tolyl)-3-(trifluoromethyl)-1H-pyrazol-1-yl)phenyl)sulfonyl)hexanamide;
- (S)-6-(2-Hydroxyguanidino)-2-propionamido-N-((4-(5-(p-tolyl)-3-(trifluoromethyl)-1H-pyrazol-1-yl)phenyl)sulfonyl)hexanamide; and
- (S)—N-(6-(2-Hydroxyguanidino)-1-oxo-1-(4-(5-(p-tolyl)-3-(trifluoromethyl)-1H-pyrazol-1-yl)phenylsulfonamido)hexan-2-yl)benzamide.

8. Compound of claim 1, wherein n is 1, 2, 3 or 4; $R^{11}$ is H or hydroxyl; and $R^{12}$ is H or acyl.

9. Compound of claim 8 wherein n is 1, 2, 3 or 4; $R^{11}$ is H or hydroxyl; and $R^{12}$ is H.

10. A pharmaceutical composition comprising a therapeutically effective amount of a compound of claim 1 and a pharmaceutically acceptable carrier.

11. The pharmaceutical composition of claim 10, further comprising a therapeutically effective amount of an active pharmaceutical ingredient selected from the group consisting of anti-inflammatory drugs, cytostatic drugs, anti-proliferative agents and angiogenesis inhibitors.

12. The pharmaceutical composition of claim 10, comprising a therapeutically-effective amount of a compound of claim 1 in a formulation suitable for parenteral administration as intravenous therapy or as an injectable to treat post-operative pain.

13. A method for treating a disease condition comprising administering to a subject in need thereof a therapeutically effective amount of a compound of claim 1, wherein the disease condition is selected from the group consisting of, actinic keratosis, cystic fibrosis, acne and a disease mediated by arginine deficiency.

14. The method of claim 13, wherein the disease condition is a disease mediated by arginine deficiency.

15. The method of claim 13, wherein the subject is a mammal.

16. A method for treating a disease condition comprising administering to a subject in need thereof a therapeutically effective amount of a compound of claim 1, wherein the disease condition is selected from the group consisting of non-small cell lung cancer, skin cancer, liver cancer, colorectal cancer, glioblastoma, squamous cell cancer, bladder cancer, breast cancer, biliary tract cancer, cervical cancer, prostate cancer, small cell lung cancer, ovarian cancer, pancreatic cancer, and gastrointestinal cancer.

17. The method of claim 16, wherein the condition is non-small cell lung cancer.

18. The method of claim 16, wherein the condition is metastatic colorectal cancer.

19. A method for healing a wound comprising administering to a subject in need thereof a therapeutically effective amount of a compound of claim 1.

* * * * *